(12) United States Patent
Chanda et al.

(10) Patent No.: US 9,523,638 B2
(45) Date of Patent: Dec. 20, 2016

(54) GAS CELL ASSEMBLY AND APPLICATIONS IN ABSORPTION SPECTROSCOPY

(71) Applicants: Unisearch Associates Inc., Concord (CA); Unisearch Instruments Nanjing Inc., Nanjing (CN)

(72) Inventors: Alak Chanda, Brampton (CA); Shimin Wu, Nanjing (CN)

(73) Assignees: Unisearch Associates Inc., Ontario (CA); Unisearch Instruments Nanjing Inc., Nanjing (CN)

( * ) Notice: Subject to any disclaimer, the term of this patent is extended or adjusted under 35 U.S.C. 154(b) by 0 days.

(21) Appl. No.: 14/737,221

(22) Filed: Jun. 11, 2015

(65) Prior Publication Data

US 2016/0069797 A1     Mar. 10, 2016

Related U.S. Application Data

(60) Provisional application No. 62/065,370, filed on Oct. 17, 2014.

(30) Foreign Application Priority Data

Sep. 7, 2014   (CN) .......................... 2014 1 0454301
Feb. 25, 2015  (CN) .......................... 2015 1 0087593

(Continued)

(51) Int. Cl.
*G01N 21/39*     (2006.01)
*G01N 21/3504*   (2014.01)
*G01N 21/03*     (2006.01)

(52) U.S. Cl.
CPC ............ *G01N 21/39* (2013.01); *G01N 21/031* (2013.01); *G01N 21/3504* (2013.01);

(Continued)

(58) Field of Classification Search
CPC .. G01N 21/39; G01N 21/3504; G01N 21/031; G01N 2021/399; G01N 2201/022; G01N 2201/0612; G01N 21/0396; G01N 21/0332

(Continued)

(56) References Cited

U.S. PATENT DOCUMENTS 3,916,185 A   10/1975  Jehly
3,916,195 A   10/1975  Burch et al.

(Continued)

FOREIGN PATENT DOCUMENTS

WO   WO-2012/142549 A1   10/2012

OTHER PUBLICATIONS

Altmann, R. et al., "Two-mirror multipass absorption cell," Applied Optics, vol. 20, No. 6, pp. 995-999 (Mar. 15, 1981).

(Continued)

*Primary Examiner* — Sang Nguyen
(74) *Attorney, Agent, or Firm* — Foley & Lardner LLP

(57) ABSTRACT

A gas cell assembly and applications of the gas cell assembly in absorption spectroscopy. An example gas cell assembly includes a gas cell body with an inlet for receiving a gas sample from a gas source; a first and a second end portions that allow optical transmission into and out of the body, the second end portion being substantially opposite from the first end portion; and a channel providing a path for the gas sample and optical beam(s) between the first end portion and the second end portion. The gas cell assembly also includes reflective surfaces outside the body to receive versions of the optical beams from the body and to reflect each version of the incident beam towards the body. A detector, then, receives a last reflected beam and transmits a corresponding data signal to a processing unit for analyzing the gas sample based on the data signal.

24 Claims, 14 Drawing Sheets

(30) Foreign Application Priority Data

Mar. 24, 2015 (CA) ..................................... 2886213
May 26, 2015 (EP) ..................................... 15169283

(52) U.S. Cl.
CPC ..... *G01N 21/0303* (2013.01); *G01N 21/0332* (2013.01); *G01N 2021/0396* (2013.01); *G01N 2021/399* (2013.01); *G01N 2201/022* (2013.01); *G01N 2201/0612* (2013.01)

(58) Field of Classification Search
USPC ........ 356/432–437, 246, 300–301, 317, 326; 250/343, 336.1, 338.1
See application file for complete search history.

(56) References Cited

U.S. PATENT DOCUMENTS

| | | | | |
|---|---|---|---|---|
| 4,180,739 | A * | 12/1979 | Abu-Shumays | G01N 21/0332 250/458.1 |
| 5,723,864 | A * | 3/1998 | Atkinson | G01N 21/3504 250/339.13 |
| 5,940,180 | A * | 8/1999 | Ostby | B23Q 1/5462 356/498 |
| 6,486,474 | B1 | 11/2002 | Owen et al. | |
| 6,717,665 | B2 * | 4/2004 | Wagner | G01N 21/21 250/461.1 |
| 8,358,417 | B2 * | 1/2013 | Feitisch | G01J 3/28 356/326 |
| 8,674,306 | B2 * | 3/2014 | Falk | G01N 21/65 250/343 |
| 8,848,192 | B2 | 9/2014 | Carmignani et al. | |
| 2002/0158202 | A1 | 10/2002 | Webber et al. | |
| 2004/0095579 | A1 * | 5/2004 | Bisson | G01N 21/1702 356/432 |
| 2005/0286054 | A1 | 12/2005 | Chen et al. | |
| 2006/0263256 | A1 | 11/2006 | Koshel et al. | |
| 2007/0242720 | A1 | 10/2007 | Eckles et al. | |
| 2015/0160126 | A1 * | 6/2015 | Carangelo | G01N 21/3504 356/437 |

OTHER PUBLICATIONS

Extended European Search Report, European App. No. 15169283.7, Unisearch Associates Inc., et al., 8 pages (Feb. 10, 2016).

McManus, J.B. et al., "Astigmatic mirror multipass absorption cells for long-path-length spectroscopy," Applied Optics, vol. 34, No. 18, pp. 3336-3348 (Jun. 20, 1995).

Barlome, R., et al., "High-temperature multipass cell for infrared spectroscopy of heated gases and vapors," Review of Scientific Instruments, American Institute of Physics, vol. 78, Issue 013110, pp. 1-6 (Jan. 22, 2007).

Borysow, Jacek, et al., "Laser Multipass system with interior cell configuration," Applied Optics, Optical Society of America, vol. 50, Issue No. 30, pp. 5812-5815 (Oct. 20, 2011).

Canadian Office Action, Canadian Patent Application No. 2,886,213, 3 pages (Jul. 2, 2015).

* cited by examiner

GAS CELL ASSEMBLY AND APPLICATIONS IN ABSORPTION SPECTROSCOPY

CROSS-REFERENCE TO RELATED APPLICATIONS

This application claims foreign priority to Chinese Patent Application No. 201410454301.1, entitled "Gas Cell Assembly and Applications in Absorption Spectroscopy", filed on Sep. 7, 2014; Chinese Patent Application No. 201510087593.4, entitled "Gas Cell Assembly and Applications in Absorption Spectroscopy", filed on Feb. 25, 2015; Canadian Patent Application No. 2,886,213, entitled "Gas Cell Assembly and Applications in Absorption Spectroscopy", filed on Mar. 24, 2015; and European Patent Application No. 15169283.7, entitled "Gas Cell Assembly and Applications in Absorption Spectroscopy", filed on May 26, 2015; and also claims the benefit of U.S. Provisional Application No. 62/065,370, entitled "Gas Cell Assembly and Applications in Absorption Spectroscopy", filed on Oct. 17, 2014. The complete disclosure of each of Chinese Patent Application No. 201410454301.1, U.S. Provisional Application No. 62/065,370, Chinese Patent Application No. 201510087593.4, Canadian Patent Application No. 2,886,213, and European Patent Application No. 15169283.7 is incorporated herein by reference.

FIELD

The described embodiments relate to a gas cell assembly and to applications of the gas cell assembly in absorption spectroscopy.

BACKGROUND

Absorption spectroscopy is often used in the content analysis of various substances. The content analysis may involve identification of the contents in the substances and/or an amount of a particular content in the substance.

In general, absorption spectroscopy includes spectroscopic techniques that measure the absorption of electromagnetic radiation as a result of the interaction of the electromagnetic radiation with one or more components of the substance. The absorption of the electromagnetic radiation is measured as a function of frequency or wavelength. The component(s) in the substance absorbs a certain amount of energy from the electromagnetic radiation. The intensity of the absorption varies due to the component(s) that are present in the substance and as a function of the frequency of the electromagnetic radiation.

SUMMARY

Various embodiments described herein generally relate to a gas cell assembly and applications of the gas cell assembly for absorption spectroscopy.

In accordance with some embodiments, there is provided a gas cell assembly comprising: a gas cell body having an inlet for receiving a gas sample from a gas source; a first end portion along a longitudinal axis of the body, the first end portion allowing optical transmission into and out of the body, and the first end portion receiving an incident beam from an optical source; a second end portion substantially opposite from the first end portion, the second end portion allowing the optical transmission into and out of the body; and a channel coupled with the inlet, a length of the channel being defined by the first end portion and the second end portion, the channel providing a path for the gas sample and at least the incident beam between the first end portion and the second end portion; one or more reflective surfaces positioned outside the body, the one or more reflective surfaces including a reflective surface substantially opposite from the second end portion, the one or more reflective surfaces receiving one or more versions of the incident beam from the body and reflecting each version of the incident beam towards the body; and a detector operable to receive, from one of the first end portion and the second end portion, a version of a last reflected beam, the last reflected beam being a reflected beam directed towards the detector by the one or more reflective surfaces, the detector being operable to transmit a data signal corresponding to the version of the last reflected beam to a processing unit for analyzing the gas sample based on the data signal.

In accordance with some embodiments, a length of the path of the incident beam is substantially defined by, at least, a length of the channel and a configuration of the one or more reflective surfaces, the configuration of the one or more reflective surfaces providing, prior to the detector receiving the last reflected beam, at least one transmission of a version of the incident beam within the channel and at least one transmission of a version of the respective reflected beam within the channel.

In accordance with some embodiments, the one or more reflective surfaces includes a first reflective surface substantially opposite from the first end portion and a second reflective surface substantially opposite from the second end portion; and the optical source further includes a source directing surface for receiving the incident beam from the optical source and directing the incident beam towards the first end portion, the source directing surface being positioned substantially between the first reflective surface and the first end portion.

In accordance with some embodiments, the one or more reflective surfaces includes a first reflective surface substantially opposite from the first end portion and a second reflective surface substantially opposite from the second end portion; and the detector further includes a detector directing surface for receiving the version of the last reflected beam from the first end portion and directing the version of the last reflected beam towards the detector, the detector directing surface being positioned substantially between the first reflective surface and the first end portion.

In accordance with embodiments where the one or more reflective surfaces includes a first reflective surface and a second reflective surface substantially opposite from the second end portion, and the first reflective surface being substantially opposite from the first end portion, the first reflective surface having: an optical source opening for receiving the incident beam from the optical source and directing the incident beam towards the first end portion; and a detector opening for receiving the version of the last reflected beam from the first end portion and directing the version of the last reflected beam towards the detector.

In accordance with some embodiments, the second reflective surface includes at least two neighbouring reflective surfaces configured to alternately reflect the one or more versions of the incident beam towards the body.

In accordance with embodiments where the one or more reflective surfaces include a first reflective surface and a second reflective surface, the first reflective surface being substantially opposite from the first end portion, the first reflective surface having an optical source opening for receiving the incident beam from the optical source and directing the incident beam towards the first end portion; and the second reflective surface being the reflective surface substantially opposite from the second end portion, the second reflective surface having a detector opening for receiving the version of the last reflected beam from the second end portion and directing the version of the last reflected beam towards the detector.

In accordance with some embodiments, the second reflective surface is adjustable for varying a position of the detector opening relative to the optical source opening, the position of the detector opening varying a number of the one or more versions of the incident beam and a number of the respective reflected beams passing through the channel.

In accordance with some embodiments, the optical source opening includes: a first optical source opening for receiving a first incident beam from the optical source; and a second optical source opening for receiving a second incident beam from the optical source; and the detector opening includes: a first detector opening for receiving the version of the last reflected beam from the second end portion and directing the version of the last reflected beam towards the detector, the version of the last reflected beam corresponding to the first incident beam; and a second detector opening for receiving a version of the second incident beam from the second end portion and directing the version of the second incident beam towards at least one of the detector and a reflector component for directing the version of the second incident beam towards the detector.

In accordance with some embodiments, the optical source includes one or more optical source components, and each of the first and second incident beams being provided by a different optical source component.

In accordance with some embodiments, the detector includes one or more detector components, and each detector opening being configured to direct the respective beams to a different detector component.

In accordance with some embodiments, the one or more detector components includes a first detector component and a second detector component positioned at a different end of the gas cell assembly than the first detector component; the first detector opening directs the version of the last reflected beam towards the first detector component; and the second detector opening directs the version of the second incident beam towards the reflector component, and the reflector component directs the version of the second incident beam towards the second detector component.

In accordance with some embodiments, the second optical source opening is provided at a substantially central location of the first reflective surface; and the second detector opening is provided at a substantially central location of the second reflective surface, the second detector opening being positioned relative from the second optical source opening to prevent any reflection of the version of the second incident beam from the second reflective surface.

In accordance with some embodiments, a section of at least one of the first end portion and the second end portion is coupled with a temperature varying material, the temperature varying material being coupled to a power supply with one or more leads; and the second optical source opening and the second detector opening are configured for receiving the one or more leads from the respective first end portion and second end portion.

In accordance with some embodiments, the optical source includes one or more optical source components; and the first incident beam includes a first multi-pass incident beam and a second multi-pass incident beam, each of the first and second multi-pass incident beams being received from a different optical source component, a path of the first multi-pass incident beam through the channel being radially offset from a path of the second multi-pass incident beam through the channel.

In accordance with some embodiments, the second reflective surface is adjustable for varying a position of the first detector opening relative to the first optical source opening, the position of the first detector opening varying a number of the one or more versions of the first incident beam and a number of the respective reflected beams passing through the channel.

In accordance with some embodiments, an orientation of the first end portion relative to the first reflective surface prevents residual optical beams at the first end portion from causing optical noise; and an orientation of the second end portion relative to the second reflective surface prevents residual optical beams at the second end portion from causing optical noise.

In accordance with some embodiments, the first end portion is oriented at a first tilt angle with respect to the longitudinal axis of the body; and the second end portion is oriented at a second tilt angle with respect to the longitudinal axis of the body, the second tilt angle being a mirror symmetry of the first tilt angle.

In accordance with some embodiments, a section of at least one of the first end portion and the second end portion is coupled with a temperature varying material.

In accordance with some embodiments, the temperature varying material comprises a heating material operable to cause a temperature of the section of the at least one of the first end portion and the second end portion to increase.

In accordance with some embodiments, the section of the at least one of the first end portion and the second end portion coupled with the temperature varying material is a substantially central location of the first end portion and the second end portion.

In accordance with some embodiments, the temperature varying material is shaped as one of a ring and a circle.

In accordance with some embodiments, the temperature varying material is coupled to a power supply with one or more leads; and at least one of the first reflective surface and the second reflective surface has a lead opening at a substantially central location, the lead opening receiving the one or more leads.

In accordance with some embodiments, the first end portion is securably coupled to the body for enclosing a first end of the body along the longitudinal axis of the body; and the second end portion is securably coupled to the body for enclosing a second end of the body, the second end being substantially opposite from the first end.

In accordance with some embodiments, each of the first end portion and the second end portion is securably coupled to the body with a respective seal.

In accordance with some embodiments, each of the first end portion and the second end portion is securably coupled to the body with a threaded coupling.

In accordance with some embodiments, each of the first end portion and the second end portion includes a transparent section allowing the optical transmission into and out of the body.

In accordance with some embodiments, the transparent section is formed of at least one of a glass material and a plastic material.

In accordance with some embodiments, each surface of the transparent section is coated with an anti-reflective material.

In accordance with some embodiments, the one or more reflective surfaces includes a mirror having a radius of curvature for the optical transmissions.

In accordance with some embodiments, the channel is substantially enclosed by a temperature varying material operable to vary a temperature of the gas sample.

In accordance with some embodiments, the temperature varying material includes a heating material operable to cause a temperature of the gas sample to be above an ambient temperature of a surrounding of the gas cell assembly.

In accordance with some embodiments, the temperature varying material includes a cooling material operable to cause a temperature of the gas sample to be below an ambient temperature of a surrounding of the gas cell assembly.

In accordance with some embodiments, the temperature varying material is operable to vary the temperature of the gas sample to a user-specified value.

In accordance with some embodiments, the incident beam includes a collimated beam.

In accordance with some embodiments, the gas cell body further includes an outlet for releasing the gas sample from the channel.

In accordance with some embodiments, the processing unit is configured to conduct an absorption spectroscopy analysis of the gas sample based on the data signal received from the detector.

In accordance with some embodiments, a wavelength of the incident beam varies according to the absorption spectroscopy analysis being conducted on the gas sample.

In accordance with some embodiments, use of an embodiment of the gas cell assembly described herein is provided for conducting an absorption spectroscopy measurement of a gas sample.

In accordance with some embodiments, there is provided an absorption spectroscopy system including: an optical source for transmitting an incident beam; a gas cell assembly having: an inlet for receiving a gas sample from a gas source; a channel coupled with the inlet, the channel providing a path for at least the incident beam and the gas sample; and a detector positioned relative to the channel for receiving a last reflected beam corresponding to a version of the incident beam, the detector being operable to transmit a data signal corresponding to the reflected beam; an absorption spectroscopy analyzer in electronic communication with the gas cell assembly, the analyzer comprising: a communication module operable to receive the data signal from the detector; and a processing module operable to conduct the absorption spectroscopy analysis of the gas sample based on the data signal; and a controller module in electronic communication with the absorption spectroscopy analyzer and the gas cell assembly, the controller module being configured to receive control signals from the absorption spectroscopy analyzer.

In accordance with some embodiments, the absorption spectroscopy system includes an embodiment of the gas cell assembly described herein.

In accordance with some embodiments, the outlet is coupled to a pump, the pump being operable to direct a movement of the gas sample from the gas source into the inlet and out of the outlet. The pump, may, in some embodiments be a jet pump.

In accordance with some embodiments, the inlet is coupled to the gas source with a sampling tube, the sampling tube being inserted into a vent opening of the gas source.

In accordance with some embodiments, a filter is provided within the sampling tube, the filter interacting with an initial gas sample from the gas source to remove contaminants from the initial gas sample for generating the gas sample.

In accordance with some embodiments, a filter is located outside the vent opening, the filter interacting with an initial gas sample from the gas source to remove contaminants from the initial gas sample for generating the gas sample.

In accordance with some embodiments, the filter includes a ceramic filter.

In accordance with some embodiments, the inlet is coupled to the sampling tube with a multi-directional valve, the multi-directional valve is operable by the controller module in a first position for providing a path between the gas source and the inlet, and in a second position for providing a path between an external gas line and the gas source.

In accordance with some embodiments, the controller module operates the multi-directional valve in the second position in response to a control signal from the absorption spectroscopy analyzer indicating the filter is to be cleaned, the path between the external gas line and the gas source directing a pressurized gas from the external gas line towards the filter.

In accordance with some embodiments, the system described herein includes a pressure measuring device coupled to the inlet, the pressure measuring device monitoring a gas pressure of the gas sample within the gas cell assembly; and a first valve operable by the controller module to provide a path between an external gas line and the filter in response to an activation signal generated by the pressure measuring device, the activation signal being generated by the pressure measuring device when the pressure measuring device determines the gas pressure is less than a minimum pressure threshold.

In accordance with some embodiments, the gas source is a power generation plant.

In accordance with some embodiments, the absorption spectroscopy analyzer is in electronic communication with the gas cell assembly via at least one of (i) one or more fiber optic cables and (ii) one or more coaxial cables.

In accordance with some embodiments, the controller module includes a relay circuitry.

BRIEF DESCRIPTION OF THE DRAWINGS

Several embodiments will now be described in detail with reference to the drawings, in which.

Figure 1:
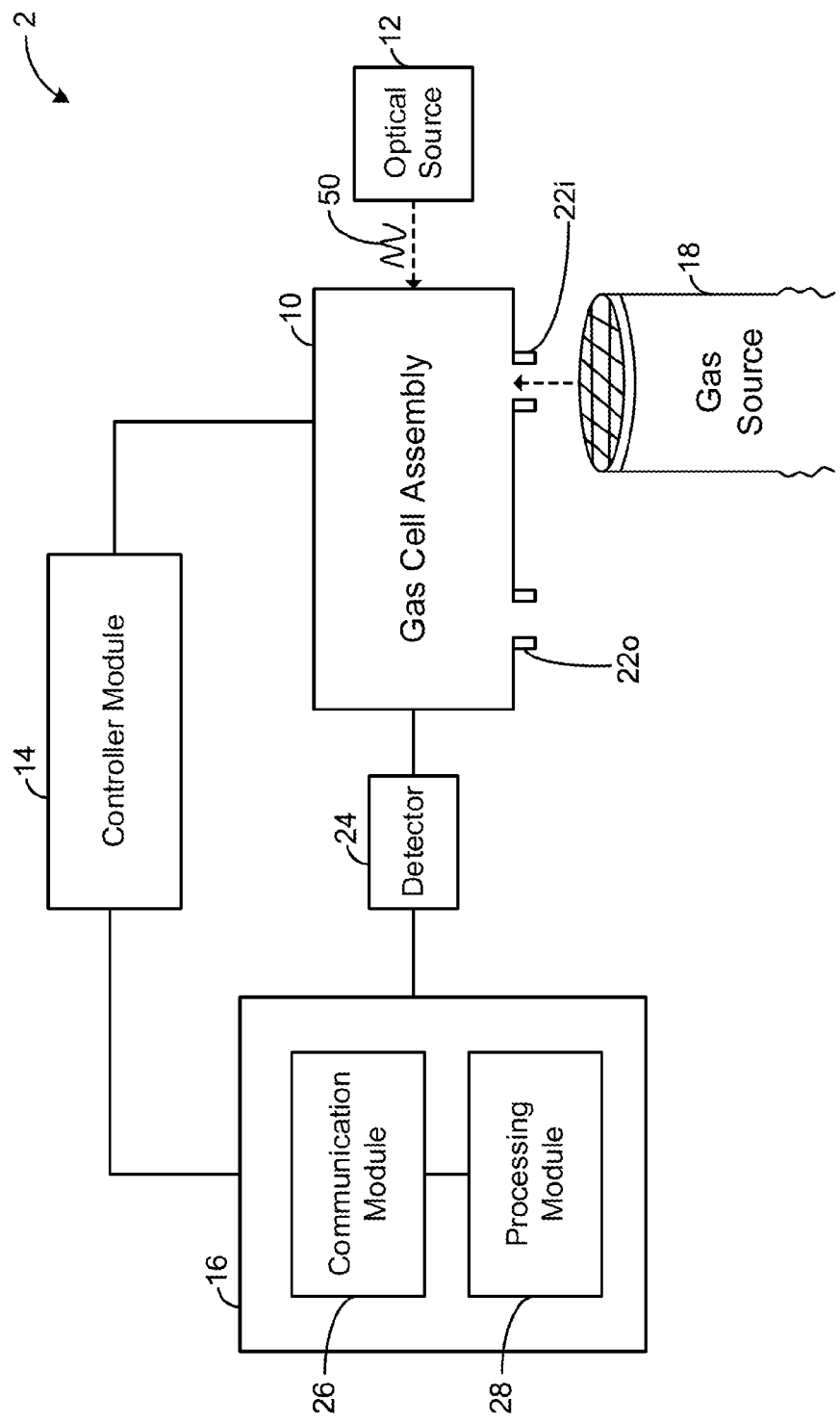
FIG. 1 is a block diagram of components interacting with a gas cell assembly in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

Optical absorption spectroscopy is an example of absorption spectroscopy and involves directing an optical beam from an optical source through the substance. The substance may be in an enclosure or an open path. The substance may be a gas, for example. As noted, the intensity of the absorption varies, at least, due to the different components that may be present in the substance. The transmitted optical beam is received by a detector, which can then provide a data signal related to the transmitted optical beam to an analyzer device for conducting the relevant absorption spectroscopy analysis.

The absorption of the electromagnetic radiation at a specific frequency by the substance can generally be quantified by the Beer-Lambert law:

$$I=I_o e^{-kcL}$$

where "I" represents an intensity of the detected optical beam, "$I_o$" represents an intensity of the initial optical beam provided by the optical source, "k" represents an absorptivity of an attenuator in the substance at a given temperature and frequency, "c" represents a concentration of the attenuator in the substance and "L" represents a path length of the optical beam through the absorbing substance. According to the Beer-Lambert law, the intensity of the detected optical beam (I) is generally inversely proportional to the path length, L, since the absorption by the substance increases as the path length increases. The inverse proportionality between the detected intensity and the path length applies especially for components within the substance that are either present at very low levels or particularly weak absorbers or both. The increased absorption can increase the sensitivity of the absorption spectroscopy analysis and, therefore, increasing the path length can be advantageous.

The sensitivity at which the contents can be identified is increasingly important in certain industries. Coal-burning power plants, for example, are becoming more regulated by the relevant regulatory bodies in terms of mono-nitrogen oxides ($NO_x$) emissions. The ability to accurately identify the contents of the substances so that appropriate feedback can be sent by the relevant control systems can therefore be critical.

The absorption of electromagnetic radiation by the substance can either be made in-situ (that is, the electromagnetic radiation is passed through the substance at the location where the substance is formed) or extractive (that is, the electromagnetic radiation is passed through the substance after the substance is extracted from its original location and brought into a measurement environment, such as a closed container). Typically, extractive absorption spectroscopy measurements are performed using an absorption cell, or a gas cell, of a suitable length. A length of the gas cell is generally restricted by practical limitations, such as portability of the gas cell and space availability at the measurement site. Multi-pass gas cells can be used for providing an increased path length that can usually improve absorption detection sensitivity without significantly increasing the size of the measurement instrument. The multi-pass gas cells typically include a set of mirrors that is exposed to the gas sample. The set of mirrors reflects the optical beam multiple times so that the path length of the optical beam through the absorbing substance increases substantially without needing to increase the length of the gas cell itself.

However, during operation of the gas cell and in particular in industrial settings, even if the gas is filtered, dust and/or other contaminants are often drawn into the gas cell. Over time, the dust and contaminants become deposited on the mirrors, and depending on the type of the contaminant, the contaminants may even react with the surfaces of the mirror. As a result, the reflectivity of the mirrors can degrade over time. It is possible that the deterioration of the mirrors can be compensated with software but will nevertheless cause a reduction in the sensitivity of the detected intensity of the optical beam. The purpose of using the multi-pass cell to increase the path length in order to increase the sensitivity of the absorption data can, therefore, be defeated. Instead, it is likely that the mirrors need to be dismantled to be cleaned or replaced. The dismantling process can be particularly cumbersome since the mirrors need to be carefully aligned.

Also, the gas cell may be required to be operated at a temperature that is well above ambient for several reasons. First, certain undesired chemicals tend to react at lower temperatures and affect the composition of the substance. The undesired chemicals may also react to form contaminants that can degrade the components of the measurement instrument. For example, in coal-burning power plants, ammonia is often injected into the resulting flue gas to reduce $NO_x$ emissions. However, over-injection of the ammonia may result in ammonia slip, or excess ammonia, within the flue gas. Depending on the temperature of the flue gas, the excess ammonia and the sulfur compounds formed during the combustion of coal can react to form ammonium bisulfate (ABS). At cooler temperatures, ABS formation can clog filters and cloud mirrors and windows of the gas cell. Second, higher temperatures may be required to prevent condensation in the gas cell from obscuring the optical beam.

The high temperature that may be required can also make the alignment of the optical components very difficult. Temperature changes can affect the alignment and, therefore, optical alignment needs to be performed when the gas cell has reached the temperature at which it will operate.

As noted, gas cells are often used for absorption spectroscopy analysis. The absorption amount and, correspondingly, the sensitivity of the absorption spectroscopy analysis can depend on a path length of the transmission of an optical beam through a sample being tested, which can be referred to as a gas sample.

Different multi-pass gas cells have been developed for increasing the path length. Common types of multi-pass cells can include gas cells based on the Herriott and White designs.

The Herriott gas cell includes two mirrors with identical focal length and the two mirrors are separated from each other by a distance, "D". The mirrors can have various forms, such as spherical, astigmatic or other complex forms. The mirrors within the Herriott gas cell are usually enclosed in a suitable container with inlet and outlet connections to allow the sample gas to flow through the gas cell at the required rate. The container used in the Herriott gas cell is usually configured to allow entry and exit of optical beams.

The White gas cell includes three spherical and concave mirrors with the same radius of curvature. Two neighbouring mirrors can be provided across from the third mirror. One of the neighbouring mirrors can be configured for receiving at least an incident beam from the optical source, and the other neighbouring mirror can be configured for, at least, directing the last reflected beam towards the detector. During the transit of the versions of the incident beam within the White gas cell, the neighbouring mirrors can alternately reflect the versions of the incident beam received from the third mirror. Similar to the Herriott gas cell, the mirrors in the White gas cell are also typically enclosed in a suitable container with inlet and outlet connections to allow the sample gas to flow through the gas cell.

However, as noted, the mirrors in the example multi-pass gas cells, such as the Herriott gas cell and the White gas cell, are in direct contact with the gas sample and are therefore, subject to any dust and/or contaminants that may be in the sample. Depending on the environment, the gas sample may include corrosive contents causing corrosion in the measurement components, such as the mirrors, of the gas cell.

Reference is first made to FIG. 1, which is a block diagram 2 of components interacting with an example gas cell assembly 10. The gas cell assembly 10 has, at least, an inlet 22i and an outlet 22o. The inlet 22i and outlet 22o may be closed to contain the gas sample within the gas cell assembly 10. As shown, the gas cell assembly 10 can receive an incident beam 50 emitted from an optical source 12. The incident beam 50 is transmitted within the gas cell assembly 10 and a version of the incident beam 50 is received by a detector 24.

Generally, although not shown in FIG. 1, the gas cell assembly 10 includes a gas cell body enclosed at a first end and a second end by a respective first end portion and a second end portion. Each of the end portions includes an optical permeable component that allows optical transmission into and out of the gas cell body, while containing the gas sample within the cell body. One or more reflective surfaces can be located substantially opposite from one of the end portions. The reflective surfaces, therefore, are not in contact with the gas sample. Embodiments of the gas cell assembly 10 will be described with reference to FIGS. 2A to 2D, 5A, 5B and 6A.

As shown in FIG. 1, the inlet 22i of the gas cell assembly 10 is operatively coupled with a gas source 18 to receive the gas sample. The detector 24 can also be in electronic communication with a computing device 16 for receiving a data signal containing data associated with the transmitted optical beam. The data associated with the transmitted optical beam may include optical data. The gas cell assembly 10 can also be in electronic communication with a controller module 14 for receiving control signals associated with the operation of the gas cell assembly 10.

When the detector 24 receives the data signal in the form of an optical signal, the detector 24 can convert the optical signal to an electrical signal. For example, the detector 24 can determine a current value that is proportional to the intensity of the transmitted optical beam received by the detector 24. The detector 24 may then provide the electrical signal to the computing device 16 via a connector, such as a coaxial cable. In some embodiments, the detector 24 may convert the electrical signal to another form, such as an optical signal using an electrical to optical signal converter. The resulting optical signal can be provided to the computing device 16 via fiber optic cables.

The detector 24 may, in some embodiments, include multiple detector components that are configured for receiving different data signals. For example, the detector 24 may include a first detector component for determining an intensity of a first optical beam and a second detector component for determining an intensity of a second optical beam that is different from the first optical beam. The various detector components may be arranged together in one unit or provided as physically separate units.

The optical source 12 is positioned relative to the gas cell assembly 10 for transmitting the incident beam 50 towards a gas cell body (not shown) containing the gas sample. A wavelength of the incident beam 50 can vary depending on the type of absorption spectroscopy analysis to be conducted and on the gas sample to be measured. That is, the wavelength may vary according to the content that is intended to be identified. For example, near or mid-infrared beams can be used for measuring various different types of gases, such as very low levels of ammonia gas. For certain other gases, visible and/or ultra-violet (UV) beams may also be used. The incident beam 50 may, in some embodiments, be a collimated beam.

The optical source 12 may include an optic generator for generating the incident beam 50 or may include launching optics that receive the incident beam 50 from a remote optic generator via fiber-optic cables.

For example, when the optical source 12 includes launching optics, the optic generator may be provided at the computing device 16. In some embodiments, the optic generator may include a tunable diode laser that is located at the computing device 16, which may be an optical spectroscopy analyzer. The incident beam 50 may therefore be a laser beam that is provided from the tunable diode laser to the optical source 12 via a fiber-optic cable that can support the wavelength of the laser beam.

Similar to the detector 24, the optical source 12 may include multiple optical source components that are configured for transmitting different incident beams 50. For example, the optical source 12 may include a first optical source component for transmitting a first incident beam and a second optical source component for transmitting a second incident beam. The various optical source components may be arranged together in one unit or provided as physically separate units. As will be described, the gas cell assembly 10 may receive multiple different incident beams 50 for identifying and/or measuring different gas components within the gas sample.

The gas source 18 can vary depending on the test environment. For example, in power generation plants, the gas source 18 may be a vent opening of a pipeline or a duct. In laboratory test environments, the gas source 18 may be an experimental gas formed from a reaction or contaminant. In chemical plants, the gas source 18 may be a process gas. In combustion applications, the gas source 18 may be an off-gas such as carbon monoxide and/or carbon dioxide. In incinerators, the gas source 18 may be a stack where, for example, hydrogen chloride needs to be measured. It will be understood that various different gas sources 18 may be used with the gas cell assemblies 10 described herein.

The computing device 16, as described, is operable to receive data signals from the detector 24 for conducting the relevant analysis on the information provided by the data signals. For example, the computing device 16 may include or may be an absorption spectroscopy analyzer for conducting an absorption spectroscopy analysis on the information provided by the data signals. The computing device 16 may include an electronic tablet device, a personal computer, workstation, server, portable computer, mobile device, personal digital assistant, laptop, smart phone, portable electronic devices, measurement instrument, or any combination of these. An optical source 12 may also be provided as part of the computing device 16. For example, the incident beam 50 from the optical source 12 can be transmitted from the computing device 16 (which may be located at a different location from the gas cell assembly 10) via a fiber-optic cable.

The computing device 16 can include, at least, a communication module 26 and a processing module 28. It should be noted that in alternative embodiments, the communication module 26 and the processing module 28 may be combined or may be separated into further modules. Furthermore, the communication module 26 and the processing module 28 may be implemented using software, hardware, or a combination of software and hardware.

The communication module 26 is operable to receive the data signals from the detector 24. The communication module 26 may include at least one of a serial port, a parallel port or a USB port. The communication module 26 may also include at least one of an Internet, Local Area Network (LAN), Ethernet, Firewire, modem, or other wireless connections. Various combinations of these elements may be incorporated within the communication module 26.

The processing module 28 is operable, at least, to conduct the relevant analysis based on the data signals received by the communication module 26, or may, in some embodiments, cause the relevant analysis to be conducted by one or more other modules (not shown). The processing module 28 may be any suitable processors, controllers or digital signal processors that can provide sufficient processing power depending on the configuration, purposes and requirements of the computing device 16. In some embodiments, the processing module 28 can include more than one processor with each processor being configured to perform different dedicated tasks.

In some embodiments, the computing device 16 may also include a storage module (not shown). The storage module can include RAM, ROM, one or more hard drives, one or more flash drives or some other suitable data storage elements such as disk drives, etc. The storage module may be internal to the computing device 16 or separate from the computing device 16 but in electronic communication with the computing device 16.

The controller module 14 can be in electronic communication with the computing device 16 and the gas cell assembly 10. Accordingly to the analysis of the information provided by the data signals, the computing device 16 can generate corresponding control signals for the controller module 14. The control signals can indicate to the controller module 14 that the operation of the gas cell assembly 10 should be varied. Example control signals will be described with reference to FIG. 8.

In some embodiments, the controller module 14 can include a relay circuitry.

In some embodiments, one or more of the gas cell assembly 10, the computing device 16 and the controller module 14 may be configured to communicate via a network (not shown) capable of carrying data. An example network may be the Internet, Ethernet, coaxial cable, fiber optics, satellite, mobile, wireless fixed line, local area network, wide area network, and others, including any combination of these, capable of interfacing with, and enabling communication between the various components.

Various embodiments of the gas cell assembly 10 will now be described with reference to FIGS. 2A to 2D, 5A, 5B and 6A.

Figure 2A:
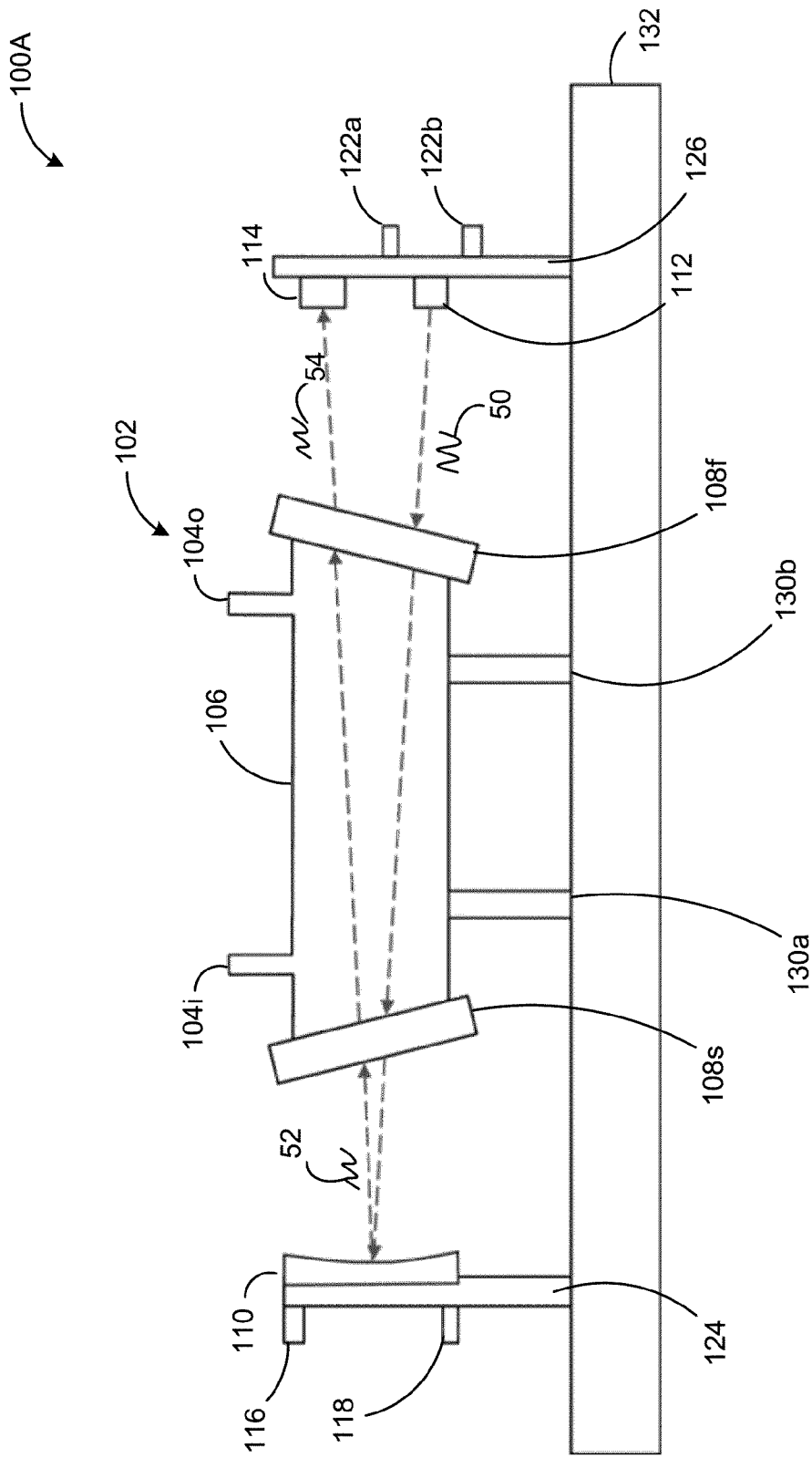
FIG. 2A is a cross-sectional view of an example gas cell assembly.

FIG. 2A is a cross-sectional view of a gas cell assembly 100A.

The gas cell assembly 100A includes a gas cell body 102 having an inlet 104*i*, an outlet 104*o*, a channel 106, a first end portion 108*f* and a second end portion 108*s*. Each of the inlet 104*i*, the outlet 104*o*, the first end portion 108*f* and the second end portion 108*s* is coupled with the channel 106. The gas cell body 102 is mounted to a base 132 with two gas cell body mounts 130*a*, 130*b*. It will be understood that other number of gas cell body mounts 130 may similarly be used for mounting the gas cell body 102 to the base 132.

The inlet 104*i* can receive the gas sample from the gas source 18 and the outlet 104*o* can release the gas sample from the channel 106.

The first end portion 108*f* is provided along a longitudinal axis of the gas cell body 102, and the second end portion 108s is substantially opposite from the first end portion 108f. The separation between the first end portion 108f and the second end portion 108s can define a length of the channel 106, as shown in FIG. 2A. The length of the channel 106 generally corresponds to the length of the gas cell assembly 100A.

Each of the first and the second end portions 108f and 108s can be securably coupled to the gas cell body 102 for enclosing a respective first end and second end of the gas cell body 102. The secured coupling may include a seal, such as o-rings, and/or a threaded coupling. Other types of couplings may similarly be used.

Each of the first and the second end portions 108f and 108s can allow optical transmission into and out of the gas cell body 102. In some embodiments, each of the first and the second end portions 108f and 108s can include a transparent section for allowing optical transmission into and out of the gas cell body 102. The transparent section should be formed of such materials that can minimize penetration losses as much as possible. An anti-reflection material may be applied to, or coated onto, each surface of the optically transparent sections to minimize reflection losses. The transparent section may be formed of a glass material, a plastic material and/or other suitable materials.

As shown in FIG. 2A, the first end portion 108f can receive the incident beam 50 from the optical source 112. The optical source 112 is mounted to the base 132 with a mount 126. The mount 126 is also coupled with two alignment controls 122a and 122b for aligning the optical source 112 with respect to the first end portion 108f and a reflective surface 110 opposite from the second end portion 108s. The alignment controls 122a, 122b may be a screw and/or other components operable to adjust an orientation of the optical source 112.

The reflective surface 110 is positioned outside the gas cell body 102. As shown in FIG. 2A, the reflective surface 110 can be mounted to the base 132 with a mount 124. The mount 124 can also be coupled with two alignment controls 116 and 118 for aligning the reflective surface 110 with respect to the second end portion 108s and the optical source 112. The two alignment controls 116, 118, like the alignment controls 122a, 122b, may also be a screw and/or other similar components that are operable to adjust an orientation of the reflective surface 110. The reflective surface 110 may be a mirror, such as a concave mirror.

When an optical beam is received at the reflective surface 110, the reflective surface 110 can reflect the optical beam, or the reflected beam 52, towards the second end portion 108s. As shown in FIG. 2A, the reflected beam 52 is received at a location of the second end portion 108s that is different from a location from which the optical beam was transmitted (a prior transmission location). The prior transmission location on the second end portion 108s is a location that previously transmitted an optical beam towards the reflective surface 110. Generally, the location at which the reflected beam 52 is received at the second end portion 108s varies, at least, according to an angle of incidence of the optical beam and a curvature of the reflective surface 110.

In the described embodiments, the second end portion 108s can be oriented relative to the reflective surface 110 and the longitudinal axis of the gas cell body 102. For example, as shown in FIG. 2A, the second end portion 108s can be tilted towards the reflective surface 110 with respect to the longitudinal axis of the gas cell body 102. The configuration of the end portions 108 relative to the reflective surfaces 110 described herein can minimize optical noise (etalons).

Generally, when an optical transparent component receives an optical beam, a small amount of the optical beam, or a residual reflection, may be reflected by the optical transparent component since the optical transparent section may act as a relatively weak reflective surface. Anti-reflection material can, to an extent, minimize the residual reflection at the optical transparent component. However, it is nevertheless still possible for the optical transparent component to generate some amount of residual reflection upon receiving the optical beam. For the gas cell assemblies 10 described herein, if the end portions 108 and the reflective surfaces 110 were not oriented in the described configurations, the end portions 108 may generate a residual reflection upon receiving a reflected beam from the reflective surface 110. The residual reflection may then arrive at the reflective surface 110 and cause an undesired series of optical beams, or optical noise (etalons). The optical noise may eventually reach the detector 114 and affect the data signals received by the detector 114.

Referring again to FIG. 2A, by orientating the second end portion 108s with respect to the reflective surface 110 and the longitudinal axis of the gas cell body 102 in certain configurations, the residual reflections may be minimized. For example, by tilting the second end portion 108s at a certain tilt angle with respect to the longitudinal axis of the gas cell body 102 and the reflective surface 110, the residual reflections that may result are prevented from being received by the reflective surface 110.

The tilt angle of each of the first and second end portions 108f, 108s can generally be equal to each other and have a mirror symmetry with each other so that the optical beam does not deviate from the path. That is, when an optical beam is received at the first end portion 108f and deviated (e.g., shifted) from the optical path by the tilt angle of the first end portion 108f, the transmitted beam received at the second end portion 108s can be realigned to the optical path by the tilt angle of the second end portion 108s. Therefore, the tilt angles at each of the respective first and second end portions 108f and 108s compensate for each other.

When the incident beam 50 is received at the first end portion 108f, a version of the incident beam 50 is transmitted towards the second end portion 108s while interacting with the gas sample inside the channel 106. The version of the incident beam 50 enters the channel 106 instead of the original incident beam 50 due to possible reflection losses at the first end portion 108f. At the second end portion 108s within the channel 106, another version of the incident beam 50, or a second version of the incident beam 50, is directed towards the reflective surface 110. The second version of the incident beam 50 is further reduced due to absorption by the gas sample while inside the channel 106 and possible reflection losses at the second end portion 108s.

In some embodiments, an anti-reflective material may be added, or coated, to one or both surfaces of each of the first end portion 108f and/or the second end portion 108s. The anti-reflective material can reduce undesirable reflections that may occur at the first end portion 108f and the second end portion 108s. The anti-reflective material may vary for different wavelengths of the optical beam and/or an angle of incidence of the optical beam. An example embodiment with the anti-reflective material will be described with reference to FIG. 2D.

The reflective surface 110 can receive the second version of the incident beam 50 and then transmits a reflected beam 52 towards the second end portion 108s. The reflected beam 52 is then transmitted through the second end portion 108s through the channel 106 towards the first end portion 108f.

The first end portion 108f then transmits a version of the reflected beam 52, or a last reflected beam 54, towards the detector 114 coupled to the mount 126. Therefore, with the gas cell assembly 100A, the various versions of the incident beam 50, combined, travel a total path length of, at least, twice the length of the channel 106 before the last reflected beam 54 is received by the detector 114. The sensitivity of the absorption measurement, therefore, is increased despite the channel 106 not having increased in length.

Also, the reflective surface 110 is not exposed to the gas sample and, therefore, will not be subjected to any contaminants and/or dust that may be present in the gas sample. Instead, the sides of the first and the second end portions 108f and 108s facing the interior of the channel 106 is exposed to the gas sample. As described, the first and the second end portions 108f and 108s can be formed of at least a transparent section to allow optical transmission into and out of the gas cell body 102. The positions of the first and the second end portions 108f and 108s, therefore, do not affect the optical alignment between the reflective surface 110 and the optical source 112. Therefore, the first and the second end portions 108f and 108s can be removed from the channel 106 for cleaning or to be replaced without affecting the alignment of the optical components, namely the reflective surface 110 and the optical source 112.

Figure 2B:
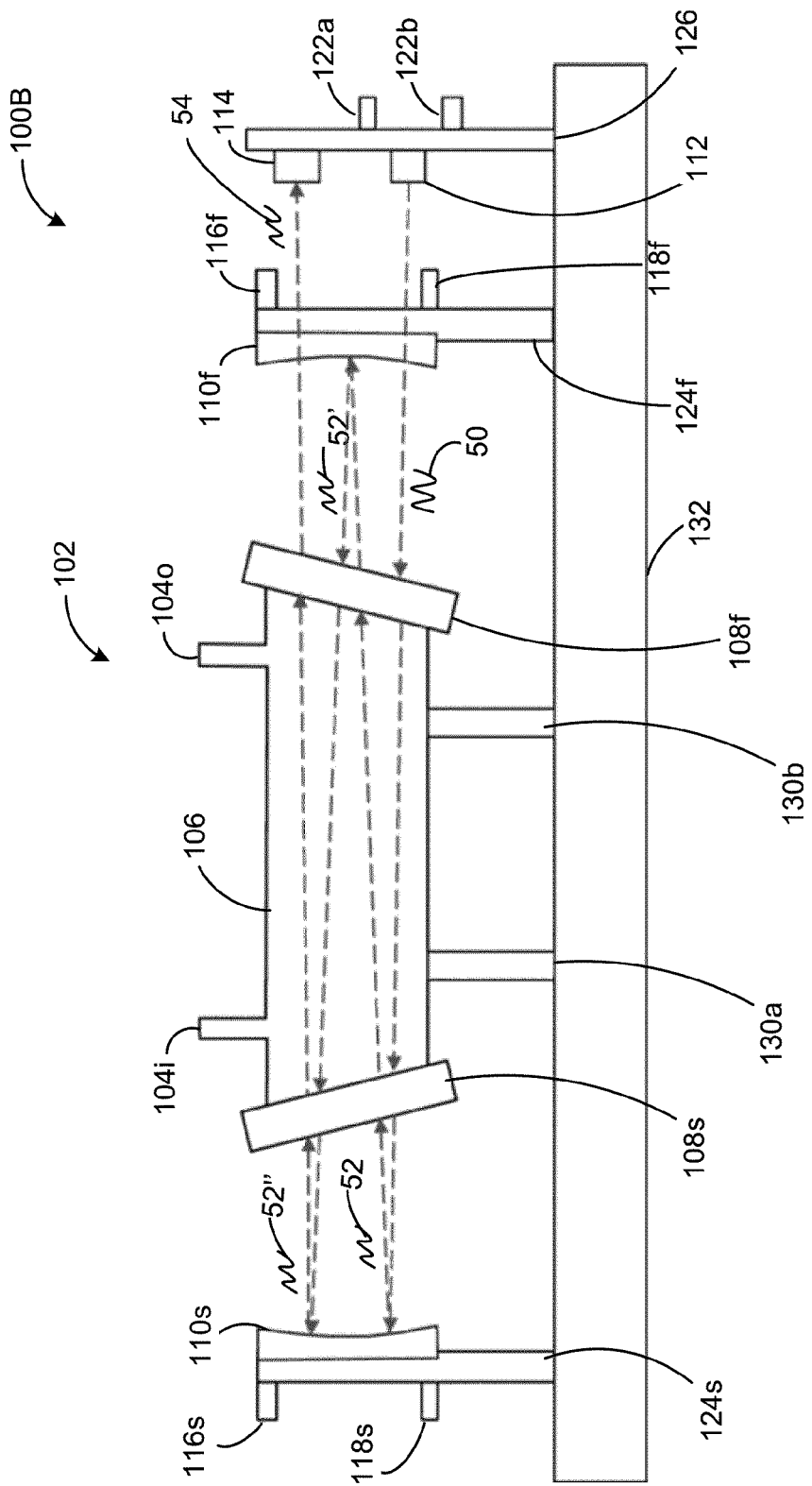
FIG. 2B is a cross-sectional view of another example gas cell assembly.

FIG. 2B is a cross-sectional view of another gas cell assembly 100B.

Unlike the gas cell assembly 100A of FIG. 2A, the gas cell assembly 100B includes two reflective surfaces, namely a first reflective surface 110f and a second reflective surface 110s. The first reflective surface 110f is positioned between the optical source 112 and the first end portion 108f, and is mounted to the base 132 with a first mount 124f. Alignment controls 116f and 118f are also coupled to the first mount 124f and are operable for adjusting an orientation of the first reflective surface 110f with respect to the first end portion 108f and the second reflective surface 110s.

The first end portion 108f can be oriented relative to the first reflective surface 110f similar to the relative orientation of the reflective surface 110 and the second end portion 108s of the gas cell assembly 100A of FIG. 2A. For example, as illustrated in FIG. 2B, the first end portion 108f may be tilted with respect to the longitudinal axis of the gas cell body 102. The second reflective surface 110s and the second end portion 108s may be similarly oriented, but having a mirror symmetry, relative to each other.

The second reflective surface 110s is similar to the reflective surface 110 of FIG. 2A. The second reflective surface 110s is mounted to the base 132 with a second mount 124s. Alignment controls 116s and 118s are also coupled to the second mount 124s for adjusting an orientation of the second reflective surface 110s with respect to the second end portion 108s and the first reflective surface 110f.

With the first and second reflective surfaces 110f and 110s, an optical beam can be transmitted multiple times through the channel 106 before being directed towards the detector 114. As shown in FIG. 2B, the incident beam 50 can be provided by the optical source 112. The first reflective surface 110f can include an optical source opening for receiving the incident beam 50.

Figures 3, 4A, 4B:
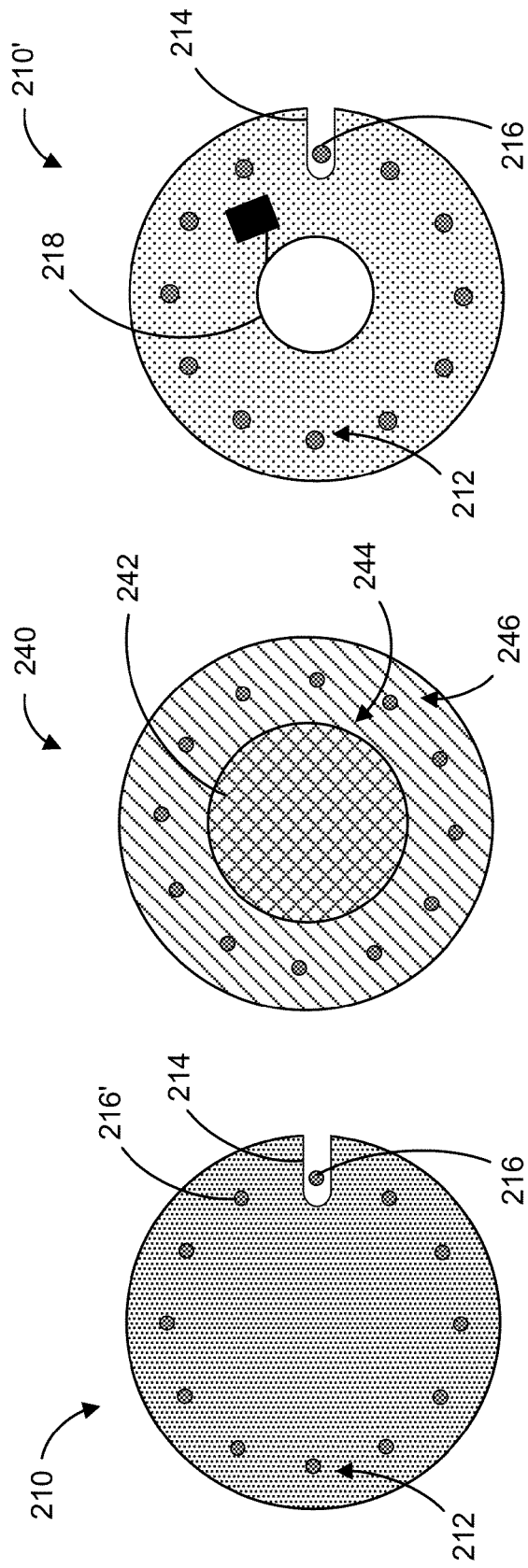
FIG. 3 is a front view of a reflective surface in accordance with an example embodiment.
FIG. 4A is a front view of an end portion of a gas cell assembly in accordance with an example embodiment.
FIG. 4B is a front view of a reflective surface in accordance with another example embodiment.

For example, as shown in FIG. 3, an example reflective surface 210 can include an opening 214 through which an optical beam 216 can be transmitted. The opening 214 may be the optical source opening in some embodiments. As shown, the opening 214 can be provided at approximately the outer perimeter of the reflective surface 210, and sized to facilitate a diameter of the optical beam.

Referring again to FIG. 2B, the optical source opening (not shown) allows for the incident beam 50 to be directed towards the first end portion 108f. As described with reference to FIG. 2A, a version of the incident beam 50 in FIG. 2B then travels through the channel 106 towards the second end portion 108s. A second version of the incident beam 50 is received at the second reflective surface 110s. A first reflected beam 52 is then generated by the second reflective surface 110s as a result of receiving the second version of the incident beam 50. The first reflected beam 52 is then directed towards the second end portion 108s and a version of the first reflected beam 52 is received at the first reflective surface 110f.

Unlike the gas cell assembly 100A of FIG. 2A, the inclusion of the first and second reflective surfaces 110f and 110s into the gas cell assembly 100B enables multiple reflections of the optical beam prior to the detector 114 receiving the last reflected beam 54. The number of reflections that may be provided by the gas cell assembly 100B can vary depending on a configuration (e.g., orientation, curvature, etc.) and separation of the reflective surfaces 110s, 110f. In the example of FIG. 2A, as shown, the first reflective surface 110f generates a second reflected beam 52', which is directed through the channel 106 towards the second reflective surface 110s. A third reflected beam 52" is generated by the second reflective surface 110s and is directed towards the gas cell body 102. A version of the third reflected beam 52", or the last reflected beam 54, is eventually directed through the first end portion 108f towards the detector 114 via a detector opening (not shown).

The detector opening may, in some embodiments, be the same as the optical source opening. The common opening 214, therefore, can be sized to facilitate the diameter of the incident beam 50 and the last reflected beam 54. The incident beam 50 received from the optical source 112 can have a different angle from the last reflected beam 54 and, therefore, the detector 114 can be located relative to the opening 214 without affecting the transmission of the incident beam 50.

In some embodiments, a reflective surface 110 may include two different openings, namely a detector opening and an optical source opening.

Accordingly, with the gas cell assembly 100B, versions of the incident beam 50, combined, travel a total path length of, at least, four times the length of the channel 106. The sensitivity of the absorption measurements for the gas sample is, as a result of multiple transmissions of the optical beam within the channel 106, increased. It will be understood that the total path length shown in FIG. 2B is merely for ease of exposition and other total path lengths may similarly be provided by the gas cell assembly 100B by adjusting the curvature of each of the reflective surfaces 110f and 110s, and a separation distance between the reflective surfaces 110f and 110s.

Figure 2C:
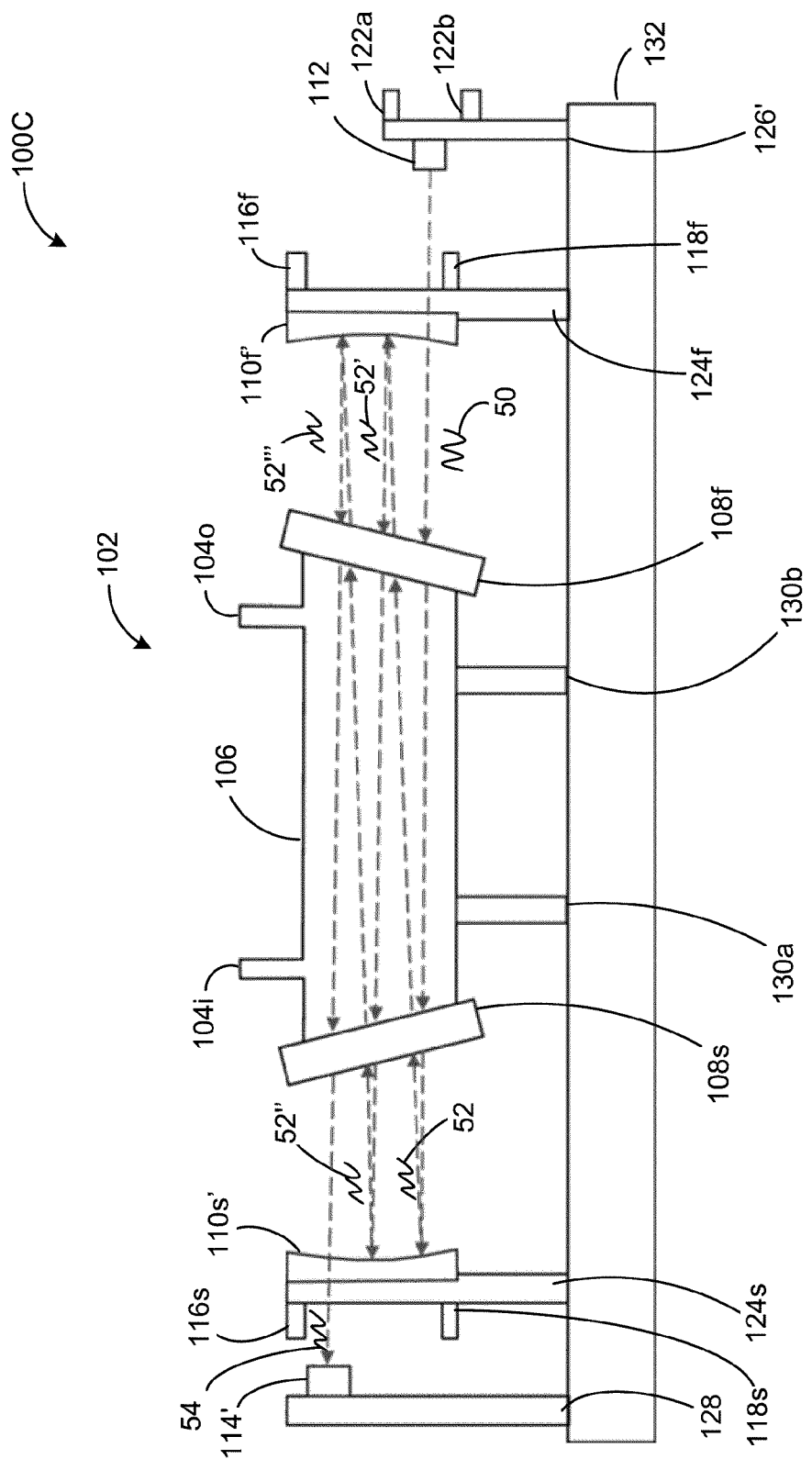
FIG. 2C is a cross-sectional view of a further example gas cell assembly.

FIG. 2C is a cross-sectional view of yet another gas cell assembly 100C.

Similar to the gas cell assembly 100B of FIG. 2B, the gas cell assembly 100C also includes two reflective surfaces, namely a first reflective surface 110f and a second reflective surface 110s'. Unlike the gas cell assembly 100B, the detector 114' of the gas cell assembly 100C is positioned to receive the last reflected beam 54 from the second reflective surface 110s via a detector opening (not shown) in the second reflective surface 110s'. As shown, the optical source 112 continues to be mounted on a mount 126' to transmit an incident beam 50 towards the first end portion 108f via an optical source opening, such as opening 214, at the first reflective surface 110f. The detector 114' can be mounted on the base 132 using a mount 128.

Each of the first reflective surface 110f and the second reflective surface 110s' may be provided as the reflective surface 210 shown in FIG. 3. When the reflective surface 210 is provided as the first reflective surface 110f, the opening 214 can be provided as the optical source opening. When the reflective surface 210 is provided as the second reflective surface 110s', the opening 214 can act as the detector opening for receiving the last reflected beam 54 and directing the last reflected beam 54 towards the detector 114'. Also shown in FIG. 3 is a series 212 of locations that received an optical beam and subsequently reflected the received optical beam away towards the gas cell body 102.

Referring again to FIG. 2C, as shown, the incident beam 50 is generated by the optical source 112 and transmitted towards the first end portion 108f via the optical source opening (not shown) in the first reflective surface 110f. A version of the incident beam 50 is eventually transmitted through the second end portion 108s and towards the second reflective surface 110s', which then generates a first reflected beam 52 towards the second end portion 108s. Multiple reflected beams 52', 52" and 52'" can be generated before the last reflected beam 54 is received at the detector 114'. The number of reflected beams 52 shown in FIG. 2C is merely for ease of exposition and it will be understood that other number of reflected beams 52 may be provided by the gas cell assembly 100C of FIG. 2C.

Generally, a separation distance between the first reflective surface 110f and the second reflective surface 110s' can be defined by a radius of curvature of the reflective surfaces 110f, 110s'. The total path length of the versions of the incident beam 50 before the last reflected beam 54 is received by the detector 114' depends on, at least, the separation distance of the reflective surfaces 110f, 110s', and/or a position of the detector opening relative to the optical source opening. Therefore, varying a position of the detector opening can vary the total path length of the versions of the incident beam 50.

For example, when the reflective surface 210 of FIG. 3 operates as the second reflective surface 110s' of FIG. 2C, the opening 214 can operate as the detector opening. The detector opening defines which of the received optical beams in the series 212 is the last reflected beam 54. In the example shown in FIG. 3, the last reflected beam 54 is the optical beam 216. To adjust the optical path, the detector opening 214 can be rotated to intercept another one of the reflected beams in the series 212 so that the other reflected beam, such as 216', becomes the last reflected beam 54. As a result of rotating the detector opening 214, one or more of the optical beams in the series 212 may no longer appear on the reflective surface 210 due to the shortening of the total path length. It will be understood that the optical beams in the series 212 are not formed consecutively and, therefore, to adjust the optical path in a controlled manner, the detector opening 214 may be rotated by varying amounts.

Figure 2D:
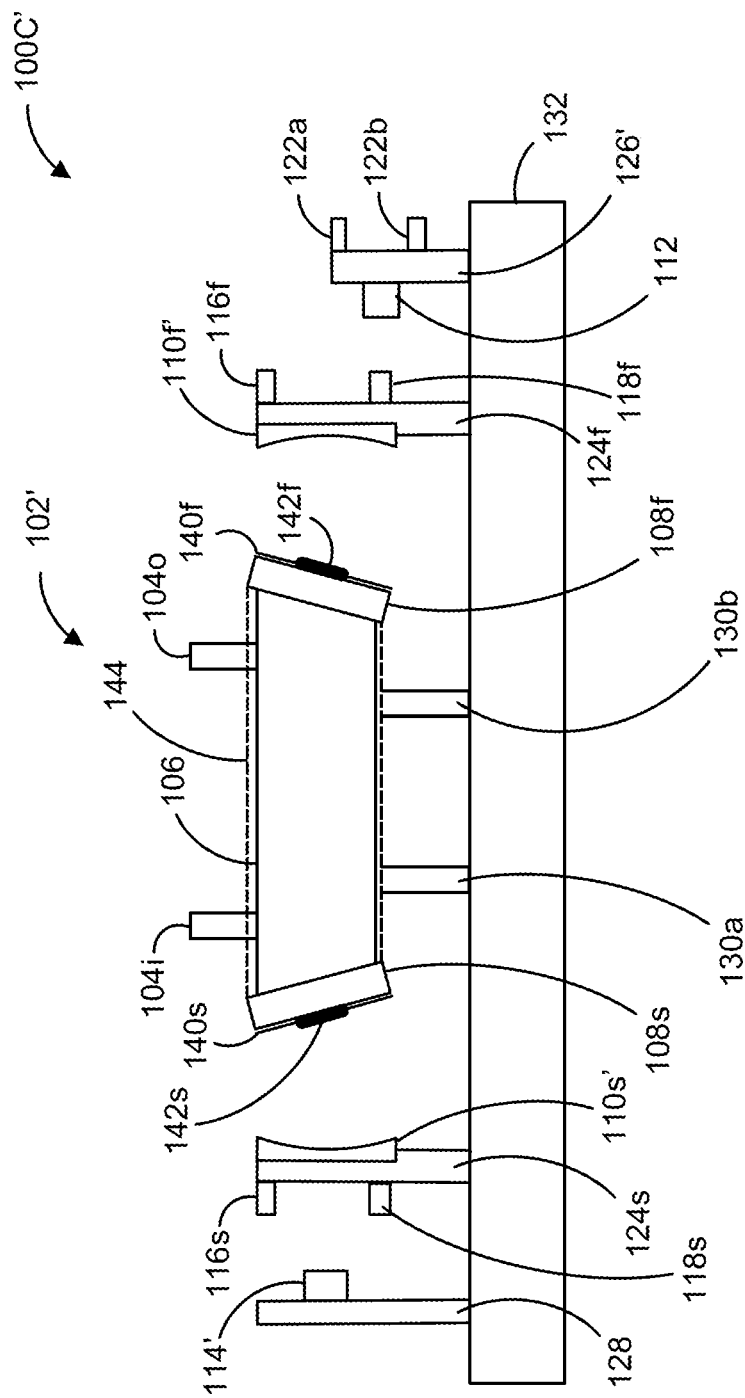
FIG. 2D is a cross-sectional view of the gas cell assembly of FIG. 2C in accordance with another example embodiment.

FIG. 2D is a cross-sectional view of another example embodiment of the gas cell assembly 100C of FIG. 2C, or gas cell assembly 100C'.

Unlike the gas cell assembly 100C, the gas cell assembly 100C' includes a temperature varying material 144 that substantially encloses the channel 106. The temperature varying material 144 may be a heating material or a cooling material.

When the temperature varying material 144 is provided as a heating material, the heating material can be operated to cause a temperature of the channel 106 to increase and as a result, the temperature of the gas sample within the channel 106 to also increase. The temperature varying material 144 may cause the temperature of the channel 106 to increase above an ambient temperature of the surrounding environment of the gas cell assembly 100C. In some embodiments, the temperature of the channel 106 may be increased by the heating material to be within a range of approximately 230° C. to 250° C. It will be understood that other temperatures may similarly be applied depending on the type of gas sample and/or analysis to be conducted on the gas sample.

When the temperature varying material 144 is provided as a cooling material, the cooling material can be operated to cause a temperature of the channel 106 to decrease and as a result, the temperature of the gas sample within the channel 106 to also decrease. In some embodiments, the cooling material may cause the temperature of the gas cell assembly 100C to be decreased below the ambient temperature of the surrounding environment of the gas cell assembly 100C.

The material with which the channel 106 is formed can also control the amount of temperature change that can be provided by the temperature varying material 144.

As described, in some embodiments, the operation of the gas cell assembly 100C' may be facilitated by increasing the temperature of the channel 106. The increased temperature can reduce formation of ABS and as a result, significantly reduce ABS deposits from being formed on the interior surfaces of the first and second end portions 108f, 108s and from clogging filters within the path of the gas sample. Also, since the temperature varying material 144 only affects the temperature of the gas cell body 102, the alignment of the optical components, namely the first and second reflective surfaces 110f and 110s', respectively, and the optical source 112, are not affected.

As described, one or both surfaces of each of the first and second end portions 108f and 108s of the gas cell assembly 100C' can include an anti-reflective material 140f, 140s, respectively. The anti-reflective material 140 can reduce undesired reflections (and thus, also reducing optical transmission losses) caused by the first and second end portions 108f and 108s.

Also, a section of the first and second end portions 108f and 108s of the gas cell assembly 100C' is coupled with a temperature varying material 142f and 142s, respectively. Similar to the temperature varying material 144, the temperature varying material 142 can operate to cause a temperature of the first end portion 108f and the second end portion 108s to increase. The temperature varying material 142 may help to reduce any condensation in the gas sample at the first and second end portions 108f and 108s, which may affect the path of the optical beam. FIG. 4A illustrates an example end portion 240 for a gas cell assembly 10.

The end portion 240 shown in FIG. 4A has a temperature varying material 242 coupled to a substantially central location, generally shown as 244. In this example, the temperature varying material 242 is provided in a circular configuration. Other configurations of the temperature varying material 242 may be used, including a ring formation. The temperature varying material 242 may be a back-adhesive tape heat source in some embodiments.

When the temperature varying material 242 is provided on the end portion 240, as shown in FIG. 4A, the corresponding reflective surface may be provided as shown in FIG. 4B. FIG. 4B illustrates an example reflective surface 210'. The reflective surface 210' is generally similar to the reflective surface 210 of FIG. 3 except that the reflective surface 210' includes a lead opening 218 for receiving leads for connecting the temperature varying material 242 at the end portion 240 to a power supply.

The lead opening 218 and the temperature varying material 242 can be provided at a generally central location of the respective end portion 240 and the reflective surface 210' when the reflective surfaces 210 are provided as concave mirrors. The concave mirrors may be spherical mirrors. Concave spherical mirrors generally operate to reflect optical beams towards an outer radial perimeter. Therefore, the location of the lead opening 218 and the temperature varying material 242 at the central location of the respective end portion 240 and the reflective surface 210' will unlikely affect the path of the optical beam in any of the described embodiments.

Some embodiments of the gas cell assemblies described herein, such as 10 and 100A to 100C', can be operated within environments having different pressures. For example, the gas cell assemblies 10 and 100A to 100C' can be operated in environments with a pressure that is below an ambient pressure of 760 Torr, such as approximately within a range of 10 Torr to 700 Torr. At lower pressures, the gas cell assemblies 10 and 100A to 100C' may allow for increased sensitivity in the measured absorption values.

Figure 5A:
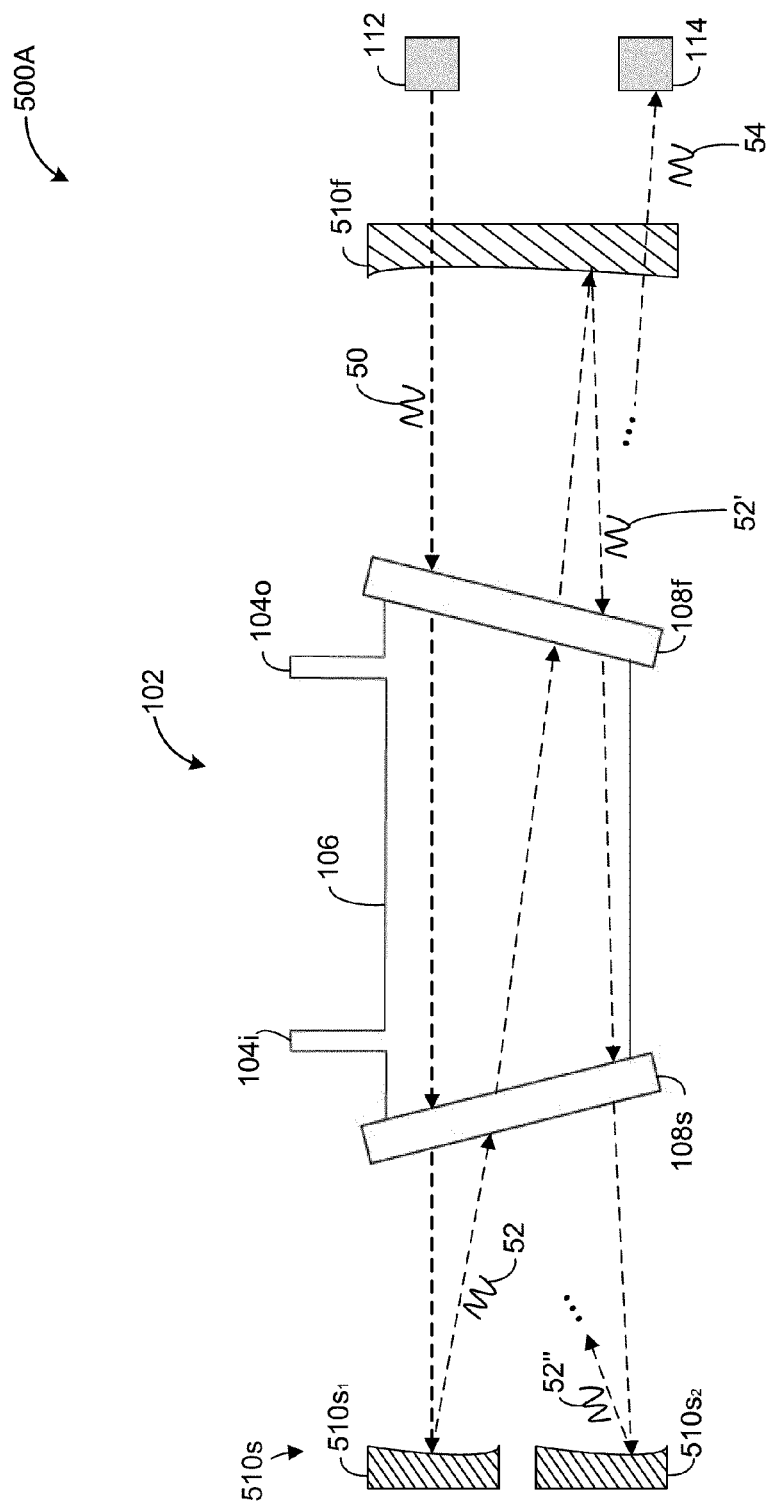
FIG. 5A is a cross-sectional view of yet another example gas cell assembly.
Figure 5B:
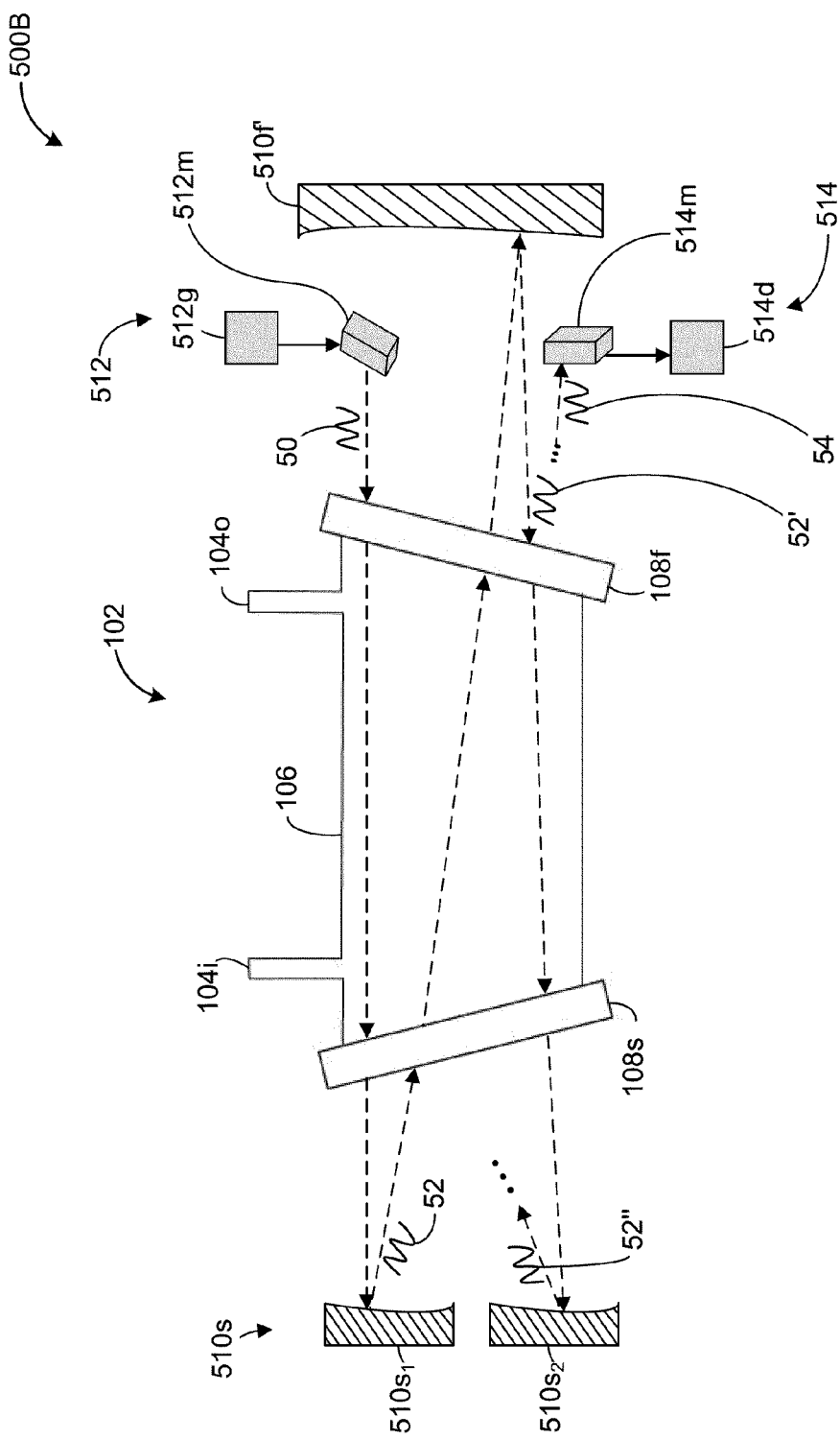
FIG. 5B is a cross-sectional view of another example gas cell assembly.

FIGS. 5A and 5B illustrate example gas cell assemblies 500A and 500B, respectively. Each of the illustrated gas cell assemblies 500A and 500B includes a second reflective surface 510s that includes two neighbouring reflective surfaces, namely $510s_1$ and $510s_2$. Also, both the optical source 112, 512 and the detector 114, 514 are positioned on the same side of the gas cell assemblies 500A, 500B as the first reflective surface 510f, 510f', respectively.

Figure 5D:
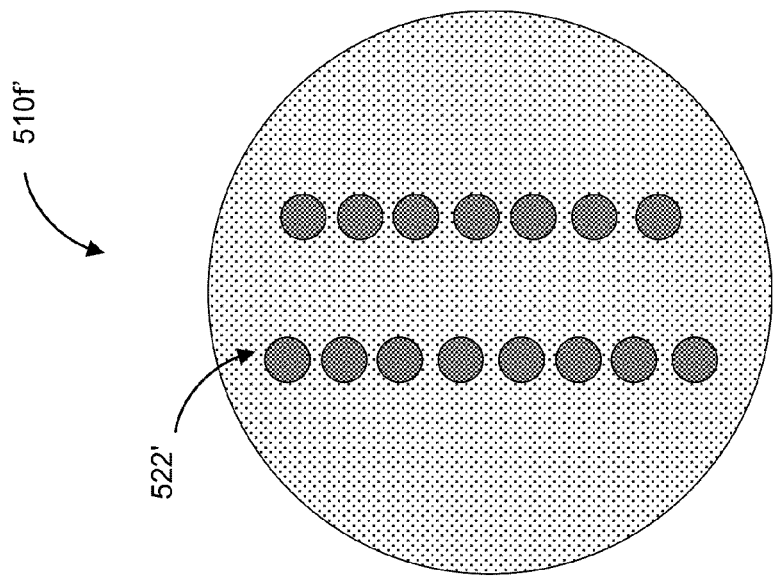
FIG. 5D is a front view of an example first reflective surface for the gas cell assembly of FIG. 5B.
Figure 5C:
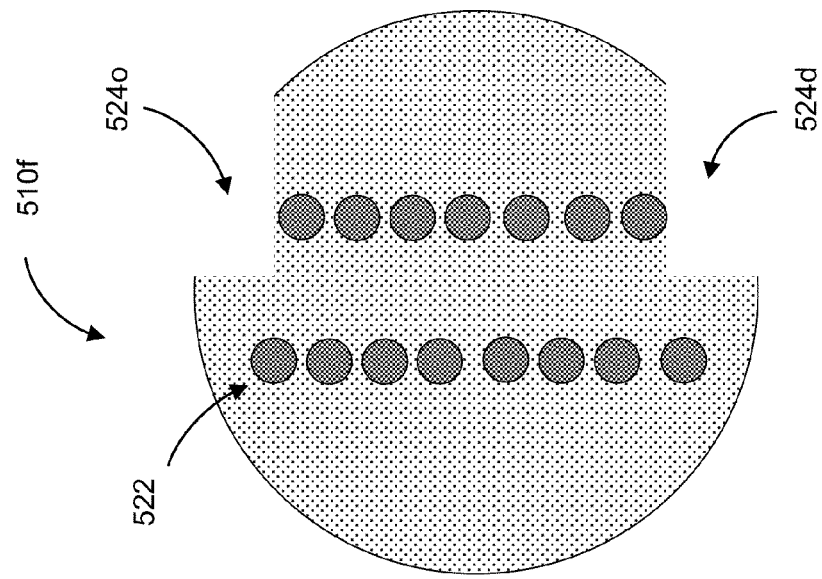
FIG. 5C is a front view of an example first reflective surface for the gas cell assembly of FIG. 5A.

As shown in FIG. 5A, the gas cell assembly 500A includes the first reflective surface 510f and the neighbouring reflective surfaces $510s_1$ and $510s_2$. Similar to the gas cell assembly 100B of FIG. 2B, the first reflective surface 510f is also positioned between the optical source 112 and the first end portion 108f, as well as between the detector 114 and the first end portion 108f. To facilitate the passage of the incident beam 50 towards the first end portion 108f and the passage of the last reflected beam 54 from the first end portion 108f, the first reflective surface 510f, as shown in FIG. 5C, can include an optical source opening 524o and a detector opening 524d, respectively.

Referring again to FIG. 5A, an example path of the incident beam 50 is illustrated. Generally, the neighbouring reflective surfaces $510s_1$ and $510s_2$ can be configured to alternately reflect the one or more versions of the incident beam 50 towards the gas cell body 102. In some embodiments, a first neighbouring reflective surface $510s_1$ can be stacked on top of a second neighbouring reflective surface $510s_2$. The first neighbouring reflective surface $510s_1$ may be placed directly on top of the second neighbouring reflective surface $510s_2$, or may be placed on top of the second neighbouring reflective surface $510s_2$ but with a separation between the neighbouring reflective surfaces $510s_1$ and $510s_2$.

For example, as shown in FIG. 5A, a version of the incident beam 50 can be received by the first neighbouring reflective surfaces $510s_1$, which then generates and directs a first reflected beam 52 towards the second end portion 108s. As the first reflective surface 510f receives a version of the first reflected beam 52, the first reflective surface 510f can then generate a second reflected beam 52' towards the first end portion 108f. A version of the second reflected beam 52' can then be received by a second neighbouring reflective surface $510s_2$ instead of the first neighbouring reflective surfaces $510s_1$. The second neighbouring reflective surfaces $510s_2$ can then generate and direct a third reflected beam 52" towards the second end portion 108s. Although not specifically shown in FIG. 5A, the first reflective surface 510f and the neighbouring reflective surfaces $510s_1$ and $510s_2$ can operate in the described manner to continue increasing a total path length of the incident beam 50. The example first reflective surface 510f shown in FIG. 5C illustrates an example series 522 of locations that received an optical beam and subsequently reflected the received optical beam towards the gas cell body 102. FIG. 5B illustrates another example gas cell assembly 500B. Similar to the gas cell assembly 500A of FIG. 5A, the gas cell assembly 500B includes a first reflective surface 510f' and the neighbouring reflective surfaces $510s_1$ and $510s_2$. However, unlike the configuration of the gas cell assembly 500A, the first reflective surface 510f' is not provided between the optical source 512 and the first end portion 108f, and between the detector 514 and the first end portion 108f. Instead, the optical source 512 and the detector 514 can be positioned away from the gas cell assembly 500B so as not to interfere with the path of each of the versions of the incident beam 50.

The optical source 512, as shown in FIG. 5B, can include a source directing surface 512m for receiving an incident beam 50 from an optic generator 512g and directing the received incident beam 50 towards the first end portion 108f. The detector 514 can include a detector directing surface 514m for receiving the last reflected beam 54 from the first end portion 108f and directing the received last reflected beam 54 towards a detecting component 514d. Each of the source directing surface 512m and the detector directing surface 514m can include a reflective surface, such as a mirror. The source directing surface 512m and the detector directing surface 514m may also be positioned substantially between the first reflective surface 510f and the first end portion 108f.

With the source directing surface 512m and the detector directing surface 514m, the first reflective surface 510f does not require openings to facilitate passage of the incident beam 50 and the last reflected beam 54. An example first reflective surface 510f is illustrated in FIG. 5D.

Figure 6A:
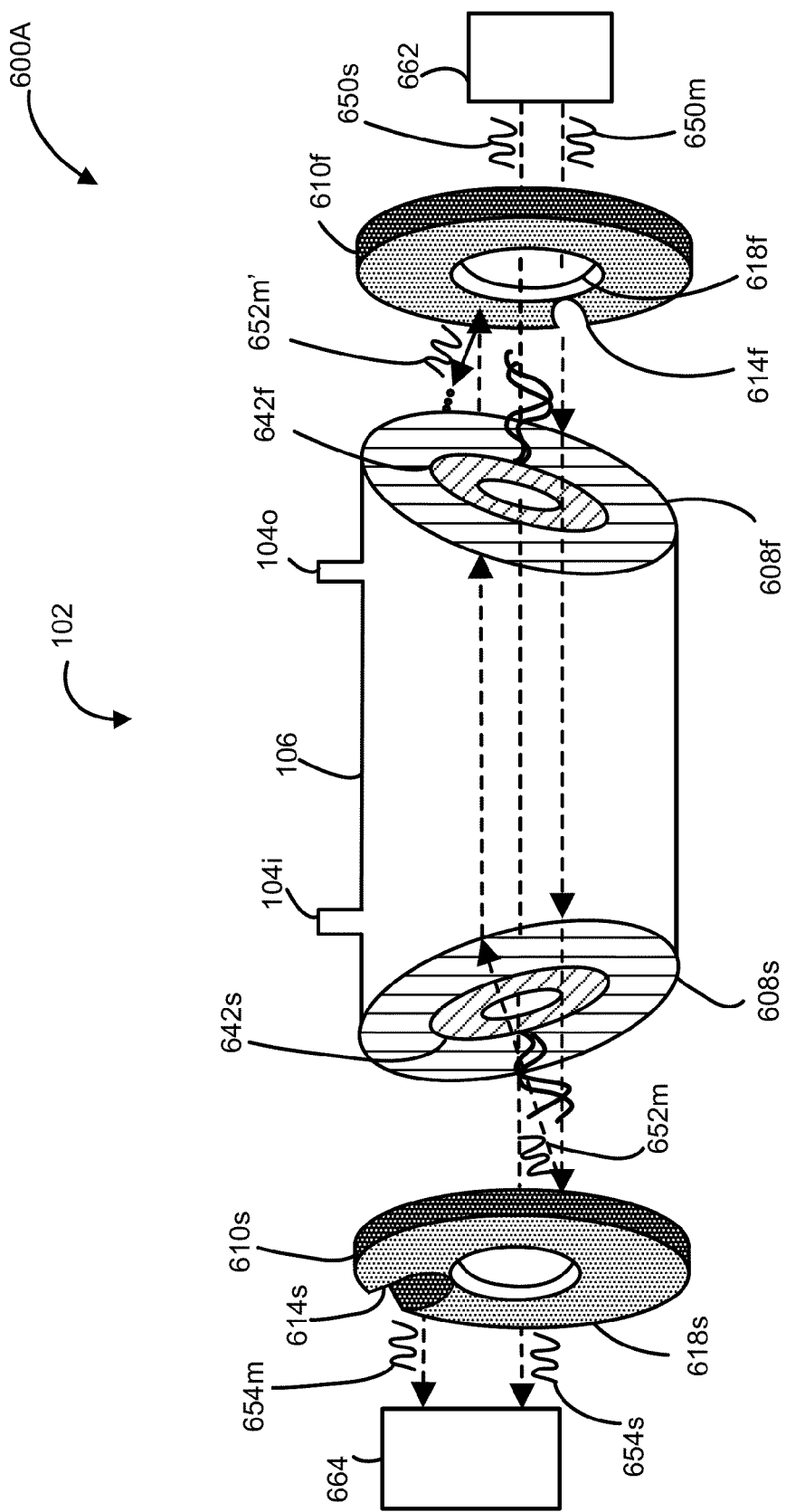
FIG. 6A is a perspective view of a gas cell assembly in accordance with another example embodiment.

Referring now to FIG. 6A, which is a perspective view of another example gas cell assembly 600A.

Similar to the gas cell assembly 100C' of FIG. 2D, the gas cell assembly 600A includes an optical source 662 and a detector 664 positioned on either ends of the gas cell assembly 600A. The optical source 662 in FIG. 6A can be configured to generate one or more different incident beams, such as first incident beam 650m and a second incident beam 650s. As described, the optical source 662 can include multiple different optic generators that are either provided together as one unit or as separate units. In some embodiments, the various different incident beams may be provided by splitting an incident beam generated by an optic generator at the optical source 662.

The different incident beams, such as 650m and 650s, can be generated by the optical source 662 and transmitted towards the gas cell body 102 for identifying different gas components in the gas sample. In some embodiments, the gas sample can include, at least, a first gas component with a low absorption intensity level (e.g., ammonia) and a second gas component with a high absorption intensity level (e.g., moisture). To facilitate detection and measurement of the first gas component, the gas cell assembly 600A can be configured to facilitate multiple passages of an optical beam, such as the first incident beam 650m, within the gas cell assembly 600A to increase the sensitivity of the detection.

The second gas component, instead, can be already associated with a high absorption intensity level and therefore, further increase in the sensitivity of the absorption intensity measurements may not be required, or may possibly be undesired since increasing the sensitivity in the detection of the second gas component may saturate the resulting data signal. For detecting and measuring the second gas component, the gas cell assembly 600A can be configured to facilitate a single passage of a corresponding optical beam, such as the second incident beam 650s, within the gas cell assembly 600A.

Figure 7B:
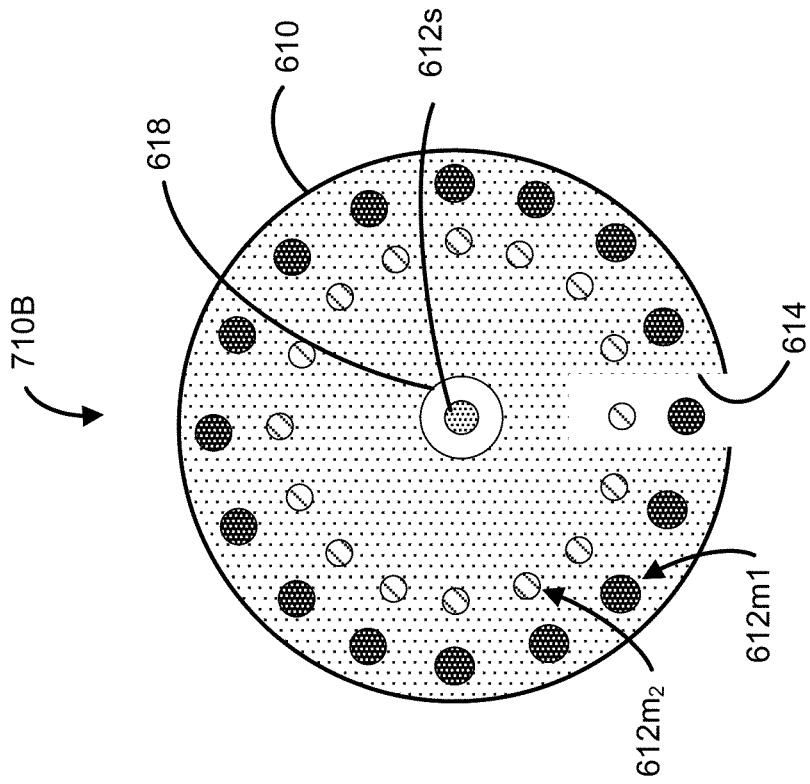
FIG. 7B is a front view of another example reflective surface for the gas cell assembly of FIGS. 6A and 6B.
Figure 7A:
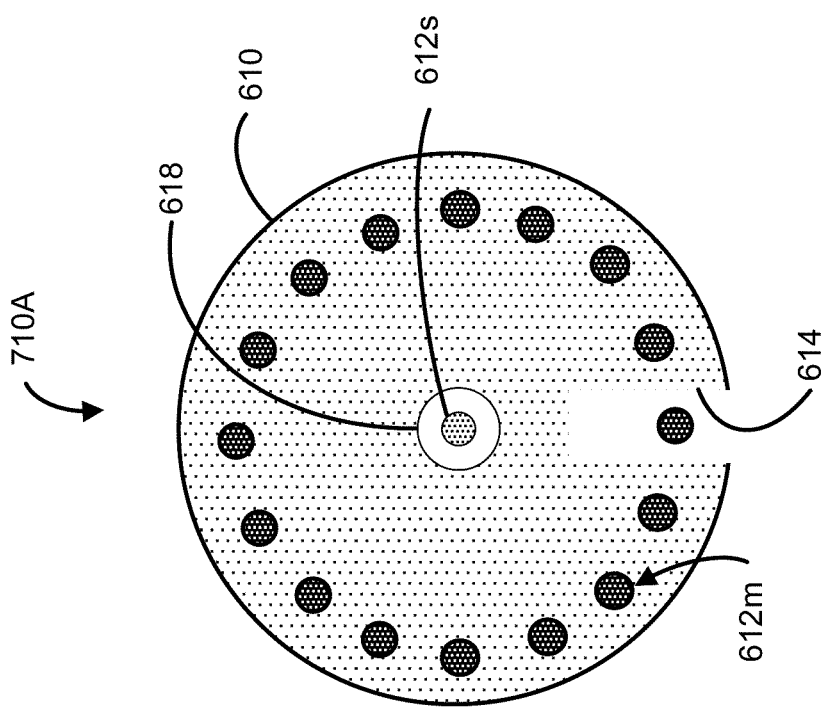
FIG. 7A is a front view of an example reflective surface for the gas cell assembly of FIGS. 6A and 6B.

As shown in FIG. 6A, the first reflective surface 610f includes a first optical source opening 614f and a second optical source opening 618f, and the second reflective surface 610s includes a first detector opening 614s and a second detector opening 618s. FIG. 7A illustrates, at 710A, an example reflective surface 610. The reflective surface 710A can include a first opening 614 (e.g., the first optical source opening 614f or the first detector opening 614s) generally at a perimeter of the reflective surface 710A and a second opening 618 (e.g., the second optical source opening 618f or the second detector opening 618s) generally at a substantially central location of the reflective surface 710A.

The first optical source opening 614f can receive the first incident beam 650m from the optical source 662 and direct the first incident beam 650m towards the first end portion 608f. The first incident beam 650m can proceed to be transmitted within the gas cell assembly 600A in a similar manner as the versions of the incident beam 50 described with respect to FIGS. 2C and 2D. For example, when the second reflective surface 610s receives a version of the first incident beam 650m, the second reflective surface 610s can then generate a first reflected beam 652m and direct the first reflected beam 652m towards the second end portion 608s. Upon receipt of a version of the first reflected beam 652m at the first reflective surface 610f, the first reflective surface 610f can generate a second reflected beam 652m'. An example series 612m of locations that received a version of the first incident beam 650m is shown on the example reflective surface 710A in FIG. 7A.

At the end of the passage of the versions of the incident beam 650m, the first detector opening 614s can receive the version of the last reflected beam 654m from the second end portion 608s and direct the version of the last reflected beam 654m towards the detector 664.

As described, the path of the second incident beam 650s can be shorter than the path of the first incident beam 650m due to the difference in the absorption intensity levels of the respective gas components for which the incident beams 650s and 650m are associated. Similar to the first optical source opening 614f, the second optical source opening 618f can receive the second incident beam 650s from the optical source 662 and direct the second incident beam 650s towards the first end portion 608f. An example passage of a version of the incident beam 650s is shown generally as 612s in FIG. 7A.

However, unlike the path of the first incident beam 650m, when a version of the second incident beam 650s arrives at the second reflective surface 610s, the version of the second incident beam 650s is not reflected by the second reflective surface 610s and instead, the version of the second incident beam 650s (or the optical beam 654s, which corresponds to the second incident beam 650s) can be directed by the second detector opening 618s towards the detector 664. As shown in FIG. 6A, the second detector opening 618s can be positioned relative to the second optical source opening 618f so as to prevent any reflection of the version of the second incident beam 650s at the second reflective surface 610s.

As shown in FIG. 7A, the path of the first incident beam 650m (illustrated generally as 612m) and the path of the second incident beam 650s (illustrated generally as 612s) do not interfere with each other since the path of the first incident beam 650m is generally along a perimeter of the reflective surfaces 610f, 610s due to a configuration of the reflective surfaces 610f, 610s, while the path of the second incident beam 650s is generally within a substantially central portion of the reflective surfaces 610f, 610s.

The detector 664 can include multiple detector components that are configured for receiving different data signals. For example, in the illustrated example of FIG. 6A, the detector 664 can include a first detector component for receiving the last reflected beam 654m from the first detector opening 614s and a second detector component for receiving the optical beam 654s from the second detector opening 618s.

In some embodiments, the gas cell assembly 600A may facilitate passage of two or more incident beams 650 that will undergo multiple reflections within the gas cell assembly 600A. For example, the first incident beam 650m can include a first multi-pass incident beam and a second multi-pass incident beam. FIG. 7B illustrates generally at 710B another example reflective surface 610 used for facilitating the path of the first multi-pass incident beam (illustrated generally as $612m_1$) and the path of the second multi-pass incident beam (illustrated generally at $612m_2$). Generally, the reflective surface 710B of FIG. 7B can be similar to the reflective surface 710A of FIG. 7A except the reflective surface 710B receives two multi-pass incident beams. As shown in FIG. 7B, the path $612m_2$ of the second multi-pass incident beam can be radially offset from the path $612m_1$ of the first multi-pass incident beam.

In some embodiments, the first and second multi-pass incident beams may be received from different optical source components.

Similar to the gas cell assembly 100C' of FIG. 2D, the first and second end portions 608f and 608s, respectively, of the gas cell assembly 600A can each include a temperature varying material 642f and 642s, respectively. It will be understood that the temperature varying material 642f and 642s are optional and are shown in FIG. 6A merely for illustrative purposes. In some embodiments, the first and second end portions 608f and 608s may be provided without the temperature varying material 642f and 642s, or one of the first and second end portions 608f and 608s may be provided with the temperature varying material 642f and 642s. The leads of the temperature varying material 642f and 642s may also be coupled to the power supply via the second optical source opening 618f and the second detector opening 618s. That is, the second optical source opening 618f and the second detector opening 618s may operate as lead openings 218.

Another example embodiment of a gas cell assembly 600B will be described with reference to FIG. 6B. Unlike the gas cell assembly 600A of FIG. 6A, the gas cell assembly 600B can facilitate passage of a second incident beam 650d, as shown. Unlike the second incident beam 650s of FIG. 6A, the second incident beam 650d of FIG. 6B is a dual pass beam.

The gas cell assembly 600B can include an optical source for generating the one or more different incident beams, and a detector for receiving data signals based on versions of the incident beams. As shown in FIG. 6B, the optical source can be provided as a first optical source component 662a for generating the second incident beam 650d and a second optical source component 662b for generating the first incident beam 650m.

The detector in the gas cell assembly 600B can include a first detector component 664a and a second detector component 664b. The first detector component 664a can receive the data associated with the last reflected beam 654m generated based on the first incident beam 650m (similar to the detector 664 of FIG. 6A), while the second detector component 664b can receive the data associated with the last reflected beam 654d generated by a reflector component 660 based on the second incident beam 650d.

Figure 6B:
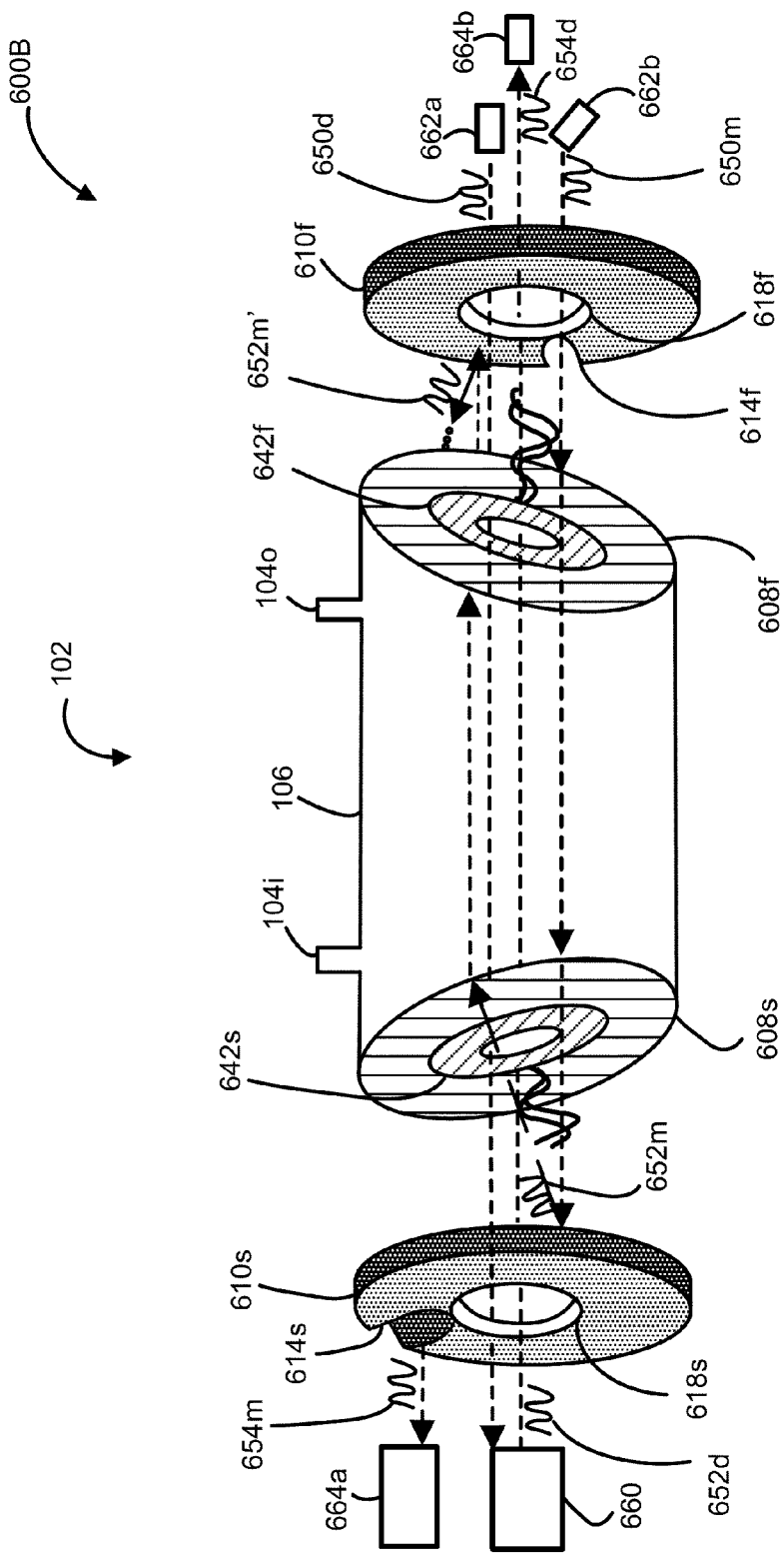
FIG. 6B is a perspective view of a gas cell assembly in accordance with yet another example embodiment.

As shown in FIG. 6B, the reflector component 660 can be positioned at a side of the second detector opening 618s that is opposite from the second end portion 608s. The reflector component 660 can be configured to receive a version of the second incident beam 650d via the second detector opening 618s from the second end portion 608s, and to provide the reflected beam 652d. The second detector component 664b can, therefore, be configured for receiving the last reflected beam 654d from the second optical source opening 618f. The reflector component 660 may generally be provided using any reflecting surface, such as, but without limitation, a plane mirror, a concave mirror, or a corner cube.

By including the reflector component 660, the second incident beam 650d may pass through the gas cell body 102 at least twice so that the resulting sensitivity of the measurements can be increased.

Figure 8:
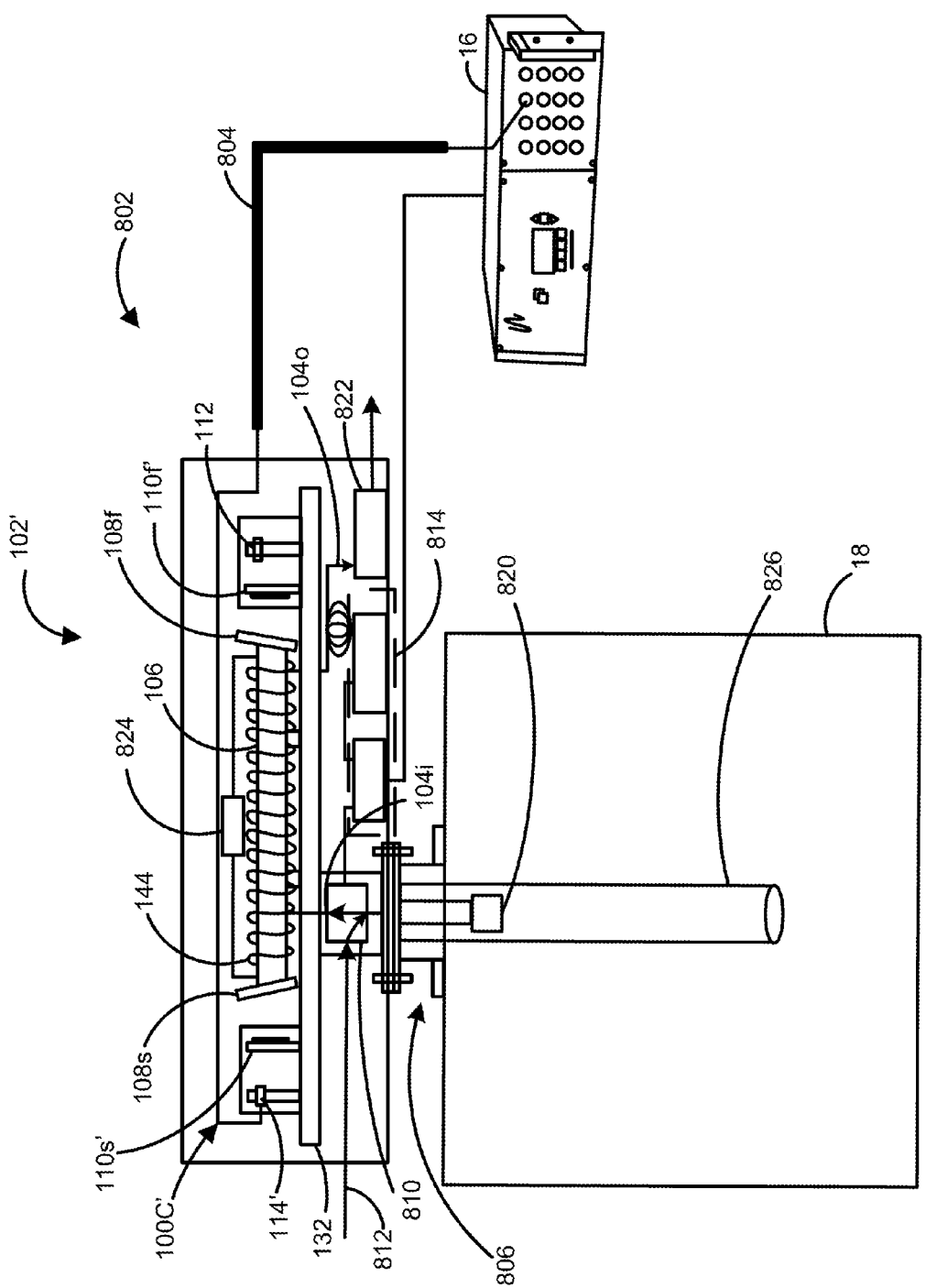
FIG. 8 illustrates an example absorption spectroscopy system involving the gas cell assembly of FIG. 2D in accordance with an example embodiment.

FIG. 8 is a block diagram of an example optical absorption spectroscopy system 802 involving, at least, the gas cell assembly 100C' of FIG. 2C. The optical absorption spectroscopy system 802 of FIG. 8 can operate as an extractive system.

The optical absorption spectroscopy system 802 is provided for a coal-burning power plant to measure an amount of ammonia in a gas sample of flue gas. It will be understood that the optical absorption spectroscopy system 802 may similarly be used for different applications. It will also be understood that the optical absorption spectroscopy system 802 can involve any of the gas cell assemblies described herein and that the gas cell assembly 100C' is used and applied in FIG. 8 as only an example.

The optical absorption spectroscopy system 802 includes an absorption spectroscopy analyzer 16 for receiving data from the gas cell assembly 100C' and for providing control signals to the gas cell assembly 100C'. The absorption spectroscopy analyzer 16 may also send an incident beam, for example a laser beam of a desired wavelength, towards the optical source 112 for launching towards the gas cell assembly 100C'. As shown in FIG. 8, the analyzer 16 is in electronic communication with the gas cell assembly 100C'. The analyzer 16 can send and receive data signals from the gas cell assembly 100C', such as the detector 114' and the optical source 112 via connectors 804, such as fiber-optic cables and/or coaxial cables. The data signals may include analog data signals. For example, the detector 114' may transmit data signals corresponding to the last reflected beam 54 to the processing module 28 of the analyzer 16 for conducting the relevant absorption spectroscopy analysis. It will be understood that other forms of electronic communication may be used. Similarly, the analyzer 16 may provide control signals to the controller module 814 that is also in electronic communication with the gas cell assembly 100C'.

The inlet 104i of the gas cell assembly 100C' can receive the flue gas from the duct of the coal-burning power plant 18 via a vent opening, generally shown as 806. The inlet 104i may receive the flue gas via different components.

For example, in some embodiments, a sampling tube 826 may couple the inlet 104i to the gas source 18. The sampling tube 826 can be inserted into the vent opening 806. The sampling tube 826 may attain the temperature of the gas sample in some embodiments. The length of the sampling tube 826 may vary depending on the size of the gas source 18 and/or the analysis to be conducted. The sampling tube 826 may also have several openings (not shown) for receiving the flue gas from the gas source 18. The openings in the sampling tube 826 may be separated from each other by a certain distance along the length and width of the sampling tube 826. The openings on the sampling tube 826 may also have different sizes depending on the analysis to be conducted on the gas sample and/or the gas source 18.

In some embodiments, a filter 820 may also be included into the sampling tube 826. The filter 820 can interact with an initial gas sample from the gas source 18 to remove dust and/or certain contaminants to generate the gas sample for the gas cell assembly 100C'. During the interaction, the filter 820 may increase in temperature. The filter 820 may attain the temperature of the gas sample in some embodiments. The filter 820 may be a ceramic filter or other suitable filter that is operable at high temperatures. The ceramic filter or other suitable filter can be associated with pore sizes that are appropriate for the gas sample.

In embodiments in which the filter 820 is provided, the inlet 104i may also be coupled to the sampling tube 814 with a multi-directional valve 810. The multi-directional valve 810 can be operated by the controller module 814. For example, the controller module 814 may operate the multi-directional valve 810 in a first position so that the multi-directional valve 810 provides a path between the gas source 18 and the inlet 104i so that the flue gas can enter the channel 106. The controller module 814 may also operate the multi-directional valve 810 in a second position to provide a path between an external gas line 812 and the gas source 18 so that a pressurized gas can be sent from the external gas line 812 towards the gas source 18 for cleaning the filter 820. The controller module 814 may operate the multi-directional valve 810 in the second position at predefined time periods and/or in response to a control signal provided by the analyzer 16 indicating the filter 820 requires cleaning.

In some embodiments, the external gas line 812 may be coupled with the inlet 104i in a further position of the multi-directional valve 810 for purging the gas sample and other particles from the channel 106.

When the flue gas is received into the channel 106 via the inlet 104i, a pump 822 may be coupled to the outlet 104o for directing the flue gas through the channel 106 towards the outlet 104o. The pump 822 may be in electronic communication with the controller module 814. For example, when the multi-directional valve 810 is at the first position (a gas sample is being received at the inlet 104i), the pump 822 can be activated by the controller module 814 to direct the gas sample towards the outlet 104o. However, when the multi-directional valve 810 is at the second position (the external gas line 812 is sending pressurized gas towards the filter 820), the pump 822 can be turned off by the controller module 814. The pump 822 may be coupled to the controller module 814 with an alternating current contactor, and the alternative current contactor can operate to turn the pump 822 on or off, depending on the operation of the multi-directional valve 810.

Also, a heat source controller 824 may also be provided to control the temperature of the temperature varying material 144 that substantially encloses the channel 106.

Figure 9:
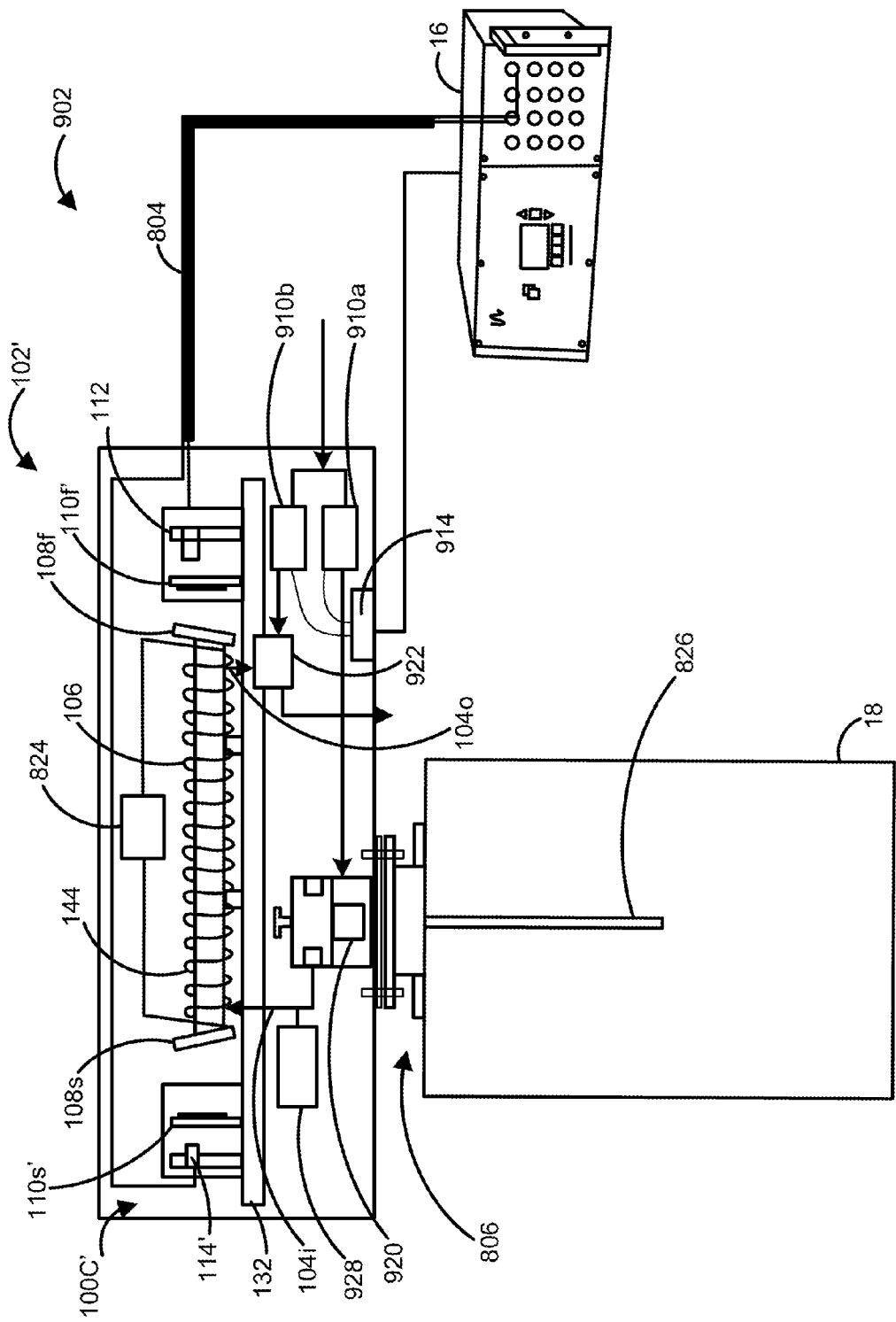
FIG. 9 illustrates another example absorption spectroscopy system involving the gas cell assembly of FIG. 2D in accordance with another example embodiment.

Referring now to FIG. 9, which is a block diagram of another example optical absorption spectroscopy system 902 involving, at least, the gas cell assembly 100C' of FIG. 2C. Similar to the optical absorption spectroscopy system 802 of FIG. 8, the optical absorption spectroscopy system 902 of FIG. 9 can also operate as an extractive system.

The optical absorption spectroscopy system 902, like the optical absorption spectroscopy system 802 of FIG. 8, is provided for a coal-burning power plant to measure an amount of ammonia in a gas sample of flue gas. It will be understood that the optical absorption spectroscopy system 902 may be used for different applications. It will also be understood that the optical absorption spectroscopy system 902 can involve any of the gas cell assemblies described herein and that the gas cell assembly 100C' is used and applied in FIG. 9 as only an example.

Like the optical absorption spectroscopy system 802 of FIG. 8, the absorption spectroscopy system 902 also includes the absorption spectroscopy analyzer 16 for receiving data from the gas cell assembly 100C' and for providing control signals to the gas cell assembly 100C', and can also receive the flue gas from the duct of the coal-burning power plant 18 via a sampling tube 826 inserted into the vent opening 806. It will be understood that the inlet 104i may receive the flue gas via different components. The absorption spectroscopy system 902 also includes a heat source controller 824 for controlling the temperature of the temperature varying material 144 that substantially encloses the channel 106.

Unlike the optical absorption spectroscopy system 802, the optical absorption spectroscopy system 902 includes a pressure measuring component 928 for monitoring a pressure of the gas sample within the channel 106, and a filter 920 outside the vent opening 806. By providing the filter 920 outside of the vent, the filter 920 can be more accessible and thus, can facilitate cleaning and/or replacement.

The pressure measuring component 928 can, in some embodiments, operate to determine whether the filter 920 is clogged and requires cleaning. The pressure measuring component 928 may be a pressure gauge. For example, when the pressure measuring component 928 detects that the gas sample within the channel 106 is below a minimum pressure threshold, the pressure measuring component 928 can determine that a surface of the filter 920 is covered with particulates such that the pressure of the gas sample is affected and therefore, the filter 920 requires cleaning. In response to the determination by the pressure measuring component 928 that the pressure of the gas sample within the channel 106 is below the minimum pressure threshold, the controller module 914 can then activate a first valve 910a to clear the surface of the filter 920. As shown in FIG. 9, the first valve 910a is operably coupled to the filter 920 so that, when activated by the controller module 914 for cleaning the surface of the filter 920, the first valve 910a facilitates passage of an external high pressure air to interact with the surface of the filter 920 for releasing the particulates.

The pump 922 in the embodiment shown in FIG. 9 can be provided as a jet pump. Similar to the pump 822, the pump 922 can, in conjunction with a second valve 910b, direct the flue gas through the channel 106 towards the outlet 104o. Similar to the channel 106, the connection lines of the pump 922 may be heated to a range of approximately 230° C. to 250° C. The increased temperature can reduce formation of ABS and as a result, significantly reduce ABS deposits from being formed on the interior surfaces of the pump 922.

The first and second valves 910a and 910b may, in some embodiments, be solenoid valves. It will be understood that other types of valves that can function in the similar fashion as described with respect to the first and second valve 910a and 910b can also be used.

As shown in and described with reference to FIG. 9, instead of using the multi-directional valve 810, the first and second valves 910a and 910b can be included into the optical absorption spectroscopy system 902 for directing gas and air flow.

Various embodiments have been described herein by way of example only. Various modification and variations may be made to these example embodiments without departing from the spirit and scope of the invention, which is limited only by the appended claims.

We claim:

1. A gas cell assembly comprising:
a gas cell body having:
an inlet for receiving a gas sample from a gas source;
a first end portion along a longitudinal axis of the body, the first end portion receiving an incident beam from an optical source and transmitting one or more versions of the incident beam into and out of the body;
a second end portion substantially opposite from the first end portion, the second end portion allowing the transmission of the one or more versions of the incident beam into and out of the body; and
a channel coupled with the inlet, a length of the channel being defined by the first end portion and the second end portion, the channel providing a path for the gas sample and at least the incident beam between the first end portion and the second end portion;
one or more reflective surfaces positioned outside the body, the one or more reflective surfaces receiving the one or more versions of the incident beam from the body and reflecting at least one of the one or more versions of the incident beam towards the body, the one or more reflective surfaces comprising:
a first reflective surface substantially opposite from the first end portion, the first reflective surface having an optical source opening for receiving the incident beam from the optical source and directing the incident beam towards the first end portion; and
a second reflective surface substantially opposite from the second end portion, the second reflective surface having a detector opening for receiving a version of a last reflected beam from the second end portion and directing the version of the last reflected beam towards a detector, the last reflected beam corresponding to a version of the incident beam reflected from the first reflective surface and intended for the detector; and
the detector operable to receive the version of the last reflected beam and to transmit a data signal corresponding to the version of the last reflected beam to a processing unit for analyzing the gas sample based on the data signal.

2. The gas cell assembly of claim 1, wherein a length of the path of the incident beam is substantially defined by, at least, a length of the channel and a configuration of the one or more reflective surfaces, the configuration of the one or more reflective surfaces providing, prior to the detector receiving the version of the last reflected beam, at least one transmission of a version of the incident beam within the channel and at least one transmission of a version of the respective reflected beam within the channel.

3. The gas cell assembly of claim 1, wherein the second reflective surface is adjustable for varying a position of the detector opening relative to the optical source opening, the position of the detector opening varying a number of the one or more versions of the incident beam and a number of the respective reflected beams passing through the channel.

4. The gas cell assembly of claim 1, wherein:
the optical source opening comprises:
a first optical source opening for receiving a first incident beam from the optical source; and
a second optical source opening for receiving a second incident beam from the optical source;
the detector opening comprises:
a first detector opening for receiving the version of the last reflected beam from the second end portion and directing the version of the last reflected beam towards the detector, the version of the last reflected beam corresponding to the first incident beam; and
a second detector opening for receiving a version of the second incident beam from the second end portion and directing the version of the second incident beam towards at least one of the detector and a reflector component for directing the version of the second incident beam towards the detector.

5. The gas cell assembly of claim 4, wherein the optical source comprises one or more optical source components, and each of the first and second incident beams being provided by a different optical source component.

6. The gas cell assembly of claim 4, wherein the detector comprises one or more detector components, and each detector opening being configured to direct the respective beams to a different detector component.

7. The gas cell assembly of claim 6, wherein:
the one or more detector components comprises a first detector component and a second detector component positioned at a different end of the gas cell assembly than the first detector component;
the first detector opening directs the version of the last reflected beam towards the first detector component; and
the second detector opening directs the version of the second incident beam towards the reflector component, and the reflector component directs the version of the second incident beam towards the second detector component.

8. The gas cell assembly of claim 4, wherein:
the second optical source opening is provided at a substantially central location of the first reflective surface; and
the second detector opening is provided at a substantially central location of the second reflective surface, the second detector opening being positioned relative from the second optical source opening to prevent any reflection of the version of the second incident beam from the second reflective surface.

9. The gas cell assembly of claim 4, wherein:
a section of at least one of the first end portion and the second end portion is coupled with a temperature varying material, the temperature varying material being coupled to a power supply with one or more leads; and
the second optical source opening and the second detector opening are configured for receiving the one or more leads from the respective first end portion and second end portion.

10. The gas cell assembly of claim 4, wherein:
the optical source comprises one or more optical source components; and
the first incident beam comprises a first multi-pass incident beam and a second multi-pass incident beam, each of the first and second multi-pass incident beams being received from a different optical source component, a path of the first multi-pass incident beam through the channel being radially offset from a path of the second multi-pass incident beam through the channel.

11. The gas cell assembly of claim 4, wherein the second reflective surface is adjustable for varying a position of the first detector opening relative to the first optical source opening, the position of the first detector opening varying a number of the one or more versions of the first incident beam and a number of the respective reflected beams passing through the channel.

12. The gas cell assembly of claim 1, wherein each of the first end portion and the second end portion comprises a transparent section allowing the optical transmission into and out of the body, and each surface of the transparent section is coated with an anti-reflective material.

13. The gas cell assembly of claim 1, wherein a section of at least one of the first end portion and the second end portion is coupled with a temperature varying material.

14. The gas cell assembly of claim 13, wherein the temperature varying material comprises a heating material operable to cause a temperature of the section of the at least one of the first end portion and the second end portion to increase.

15. The gas cell assembly of claim 13, wherein the section of the at least one of the first end portion and the second end portion coupled with the temperature varying material is a substantially central location of the first end portion and the second end portion.

16. The gas cell assembly of claim 1, wherein the channel is substantially enclosed by a temperature varying material operable to vary a temperature of the gas sample.

17. The gas cell assembly of claim 16, wherein the temperature varying material comprises a heating material operable to cause a temperature of the gas sample to be above an ambient temperature of a surrounding of the gas cell assembly.

18. The gas cell assembly of claim 16, wherein the temperature varying material comprises a cooling material operable to cause a temperature of the gas sample to be below an ambient temperature of a surrounding of the gas cell assembly.

19. A gas cell assembly comprising of claim 1, wherein:
a gas cell body having:
an inlet for receiving a gas sample from a gas source;
a first end portion along a longitudinal axis of the body, the first end portion receiving an incident beam from an optical source and transmitting one or more versions of the incident beam into and out of the body;
a second end portion substantially opposite from the first end portion, the second end portion allowing the transmission of the one or more versions of the incident beam into and out of the body; and
a channel coupled with the inlet, a length of the channel being defined by the first end portion and the second end portion, the channel providing a path for the gas sample and at least the incident beam between the first end portion and the second end portion;
one or more reflective surfaces positioned outside the body, the one or more reflective surfaces comprises a first reflective surface substantially opposite from the first end portion and a second reflective surface substantially opposite from the second end portion, the one or more reflective surfaces receiving the one or more versions of the incident beam from the body and reflecting at least one of the one or more versions of the incident beam towards the body; and a detector operable to receive, from one of the first end portion and the second end portion, a version of a last reflected beam, the last reflected beam being a reflected beam directed towards the detector by the one or more reflective surfaces, the detector being operable to transmit a data signal corresponding to the version of the last reflected beam to a processing unit for analyzing the gas sample based on the data signal, wherein at least one of:

the optical source comprises a source directing surface for receiving the incident beam from the optical source and directing the incident beam towards the first end portion, the source directing surface being positioned substantially between the first reflective surface and the first end portion; and the detector comprises a detector directing surface for receiving the version of the last reflected beam from the first end portion and directing the version of the last reflected beam towards the detector, the detector directing surface being positioned substantially between the first reflective surface and the first end portion.

20. The gas cell assembly of claim 19, wherein the second reflective surface comprises at least two neighbouring reflective surfaces configured to alternately reflect the one or more versions of the incident beam towards the body.

21. A gas cell assembly comprising:
a gas cell body having:
an inlet for receiving a gas sample from a gas source;
a first end portion along a longitudinal axis of the body, the first end portion receiving an incident beam from an optical source and transmitting one or more versions of the incident beam into and out of the body;
a second end portion substantially opposite from the first end portion, the second end portion allowing the transmission of the one or more versions of the incident beam into and out of the body; and
a channel coupled with the inlet, a length of the channel being defined by the first end portion and the second end portion, the channel providing a path for the gas sample and at least the incident beam between the first end portion and the second end portion;
one or more reflective surfaces positioned outside the body, the one or more reflective surfaces receiving the one or more versions of the incident beam from the body and reflecting at least one of the one or more versions of the incident beam towards the body, the one or more reflective surfaces comprises (i) a first reflective surface substantially opposite from the first end portion and (ii) a second reflective surface substantially opposite from the second end portion, the first reflective surface having:
an optical source opening for receiving the incident beam from the optical source and directing the incident beam towards the first end portion; and
a detector opening for receiving a version of a last reflected beam from the first end portion and directing the version of the last reflected beam towards the detector; and a detector operable to receive the version of the last reflected beam and to transmit a data signal corresponding to the version of the last reflected beam to a processing unit for analyzing the gas sample based on the data signal.

22. The gas cell assembly of claim 21, wherein:
an orientation of the first end portion relative to the first reflective surface prevents residual optical beams at the first end portion from causing optical noise; and
an orientation of the second end portion relative to the second reflective surface prevents residual optical beams at the second end portion from causing optical noise.

23. The gas cell assembly of claim 22, wherein:
the first end portion is oriented at a first tilt angle with respect to the longitudinal axis of the body; and
the second end portion is oriented at a second tilt angle with respect to the longitudinal axis of the body, the second tilt angle being a mirror symmetry of the first tilt angle.

24. A gas cell assembly comprising
a gas cell body having:
an inlet for receiving a gas sample from a gas source;
a first end portion along a longitudinal axis of the body, the first end portion receiving an incident beam from an optical source and transmitting one or more versions of the incident beam into and out of the body;
a second end portion substantially opposite from the first end portion, the second end portion allowing the transmission of the one or more versions of the incident beam into and out of the body; and
a channel coupled with the inlet, a length of the channel being defined by the first end portion and the second end portion, the channel providing a path for the gas sample and at least the incident beam between the first end portion and the second end portion;
one or more reflective surfaces positioned outside the body, the one or more reflective surfaces including a reflective surface substantially opposite from the second end portion, the one or more reflective surfaces receiving the one or more versions of the incident beam from the body and reflecting at least one of the one or more versions of the incident beam towards the body, wherein:
at least one of the one or more reflective surfaces has a lead opening at a substantially central location; and
a section of at least one of the first end portion and the second end portion is coupled with a temperature varying material, the temperature varying material is coupled to a power supply with one or more leads; and the lead opening receiving the one or more leads; and a detector operable to receive, from one of the first end portion and the second end portion, a version of a last reflected beam, the last reflected beam being a reflected beam directed towards the detector by the one or more reflective surfaces, the detector being operable to transmit a data signal corresponding to the version of the last reflected beam to a processing unit for analyzing the gas sample based on the data signal.

* * * * *

UNITED STATES PATENT AND TRADEMARK OFFICE
CERTIFICATE OF CORRECTION

PATENT NO.         : 9,523,638 B2                                    Page 1 of 1
APPLICATION NO.    : 14/737221
DATED              : December 20, 2016
INVENTOR(S)        : Alak Chanda et al.

It is certified that error appears in the above-identified patent and that said Letters Patent is hereby corrected as shown below:

In the Claims

Column 28, Claim 19, Line 46:
"A gas cell assembly comprising of claim 1, wherein:"

Should read:
"A gas cell assembly comprising:"

Signed and Sealed this
Thirtieth Day of May, 2017

Michelle K. Lee
*Director of the United States Patent and Trademark Office*